United States Patent
Node et al.

(10) Patent No.: US 6,486,323 B1
(45) Date of Patent: Nov. 26, 2002

(54) PROCESS FOR PRODUCING OPTICALLY ACTIVE TROPINONEMONOCARBOXYLIC ACID DERIVATIVE

(75) Inventors: Manabu Node, Hirakata (JP); Soichi Nakamura, Sodegaura (JP); Daisaku Nakamura, Ichihara (JP)

(73) Assignee: Nihon Medi-Physics Co., Ltd., Hyogo-ken (JP)

( * ) Notice: Subject to any disclaimer, the term of this patent is extended or adjusted under 35 U.S.C. 154(b) by 0 days.

(21) Appl. No.: 09/806,592

(22) PCT Filed: Jul. 12, 1999

(86) PCT No.: PCT/JP99/03754

§ 371 (c)(1),
(2), (4) Date: Mar. 30, 2001

(87) PCT Pub. No.: WO00/18946

PCT Pub. Date: Apr. 6, 2000

(30) Foreign Application Priority Data

Sep. 30, 1998 (JP) ............................................. 10-277868

(51) Int. Cl.$^7$ ...................... C07D 451/02; C07D 451/10

(52) U.S. Cl. ......................... 546/124; 546/127; 546/130

(58) Field of Search ................................ 546/124, 127, 546/130

(56) References Cited

FOREIGN PATENT DOCUMENTS

WO            96/39198     *  5/1996

OTHER PUBLICATIONS

Clifford E. Berkman, et al "Stereoselective Inhibition of Human Butyrylcholinesterase by Phosphonothiolate Analogs of (+) –and (−) –Cocaine", Biochemical Pharmacology (1997) vol. 54, No. 11, 1261–1266.

Anita H. Lewin, et al "A Practical Synthesis of (+) – Cocaine", J. Heterocyclic Chem (1987) vol. 24, No. 19, PP. 19–21.

* cited by examiner

Primary Examiner—Alan L. Rotman
Assistant Examiner—Rita Desai
(74) Attorney, Agent, or Firm—Sughrue Mion, PLLC

(57) ABSTRACT

An optically active tropinonemonocarboxylic acid ester derivative useful as an intermediate for synthesis of optically active tropane derivatives was obtained by reacting succindialdehyde with an organic amine and acetonedicarboxylic acid ester to obtain a tropinonedicarboxylic acid ester derivative, and then subjecting this derivative to enzyme-catalyzed asymmetric dealkoxy-carbonylation. Since anhydroecgonine methyl ester derived from the optically active tropinone-monocarboxylic acid ester derivative by reduction and dehydration had the same direction of optical rotation as in the case of anhydroecgonine methyl ester obtained from natural cocaine, it was proved that the obtained optically active tropinonemonocarboxylic acid ester derivative had the same absolute configuration as that of natural cocaine. The yield of the optically active tropinonemonocarboxylic acid ester derivative from the asymmetric dealkoxycarbonylation was 30 to 50 mol %, and its optical purity was 70 to 97% ee. In addition, it was found that a crystalline optically active anhydroecgonine carboxylic acid ester derivative can be obtained by reducing and then dehydrating the optically active tropinonemonocarboxylic acid ester derivative and that its optical purity can easily be increased by recrystallization.

10 Claims, No Drawings

PROCESS FOR PRODUCING OPTICALLY ACTIVE TROPINONEMONOCARBOXYLIC ACID DERIVATIVE

TECHNICAL FIELD

This invention relates to a process for producing an optically active tropinonemonocarboxylic acid ester derivative which is an intermediate for synthesis of alkaloids having the same optically active tropane skeleton as the skeleton of cocaine having affinity for dopamine receptors or dopamine transporters as a pharmacological action.

BACKGROUND ART

In recent years, as the span of human life extends, patients with psychoneurotic diseases such as Parkinson's disease, Alzheimer's disease, etc. increase rapidly with a growth of the aged population, and the investigation of the cause of these psychoneurotic diseases and the establishment of therapeutic methods for them are accelerated at present. Parkinson's disease is chronic and progressive and their main symptoms are tremor, myoatrophy, akinesia, and impediment in posture maintenance. This diseases is caused by the loss of the balance between dopaminergic nervous system and cholinergic nervous system which is attributable to a marked decrease in the dopamine content of the striata body and substantia nigra of extrapyramidal motor system.

Therefore, in order to treat, for example, Parkinson's disease, it is necessary to supply the dopamine deficiency or control the cholinergic nervous system in an excited state.

On the other hand, cocaine is an alkaloid contained in leaves of, for example, Erythroxylon coca of South America growth, and was clinically used as a local anesthetic in 1877 for the first time by Koller. Cocaine has recently been found to have affinity for dopamine receptors or dopamine transporters, and it is being revealed that cocaine derivatives are useful as various tracer ligands. The basic structure of cocaine is its tropane skeleton. When cocaine is used as a starting material for a cocaine derivative, an optically active tropane skeleton having the same absolute configuration as that of the skeleton of natural (−)-cocaine can easily be derived as shown in the following reaction scheme A (A. P. Kozikowski, J. Med. Chem. 1995, 38, 3086):

Reaction scheme A

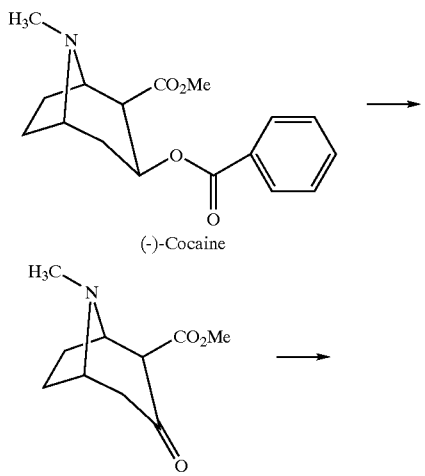

(−)-Cocaine

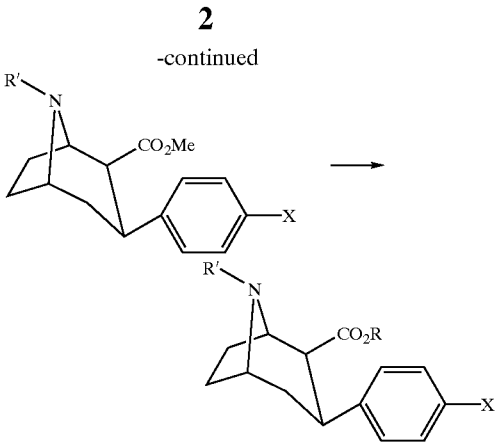

As derivatives thus synthesized by using (−)-cocaine as a starting material, there are, for example, 2β-carbomethoxy-3β-(4-iodophenyl)-tropane (β-CIT; U.S. Pat. No. 5,310,912) and its derivative 2β-carbomethoxy-3β-(4-iodophenyl)-8-(3-fluoropropyl)-nortropane (β-CIT-FP; WO 96/39198) which have affinity for dopamine transporters and are noted as diagnostic drugs for Parkinson's disease; (−)-ferruginine, an agonist for nicotine-like acetylcholine receptors; and (+)-knightinol.

Cocaine, however, is designated as a narcotic because of problems such as drug dependence, and there are various difficulties in obtaining and handling cocaine. Therefore, it is desirable to develop an economical and easy synthetic process of a cocaine analogue.

Attempts have been made to synthesize cocaine analogues since early times. Robinson et al. synthesized tropinone by condensing succindialdehyde with methyl amine and ethyl acetonedicarboxylate (Robinson R., J. Chem. Soc. 1917, 762–768). In 1991, anhydroecgonine methyl ester was synthesized from vinyldiazomethane and a pyrrole derivative by using a rhodium catalyst (Hum M. L. Davies et al., J. Org. Chem. 1991, 56, 5696–5700, Japanese Patent Application Kohyo No. 7-504665). The cocaine analogues synthesized by these processes are not optically active. As the synthesis of an optically active cocaine analogue, there is a case where (R)-allococaine or (R)-allopseudococaine was synthesized by saponifying cocaine or using as an intermediate, (R)-pseudoecgonine methyl ester obtained by optical resolution of (RS)-2-carbomethoxy-3-tropinone (F. I. Carroll et al., J. Med. Chem. 1991, 34, 883–886).

An example of enantio-selective asymmetric reaction without optical resolution is the syntheses of an optically active tropinonemonocarboxylic acid ester and anhydro-ecgonine methyl ester by the asymmetric synthetic reaction of tropinone with chiral lithium amide (Majewski M., J. Org. Chem. 1995, 60, 5825–5830). The thus obtained anhydro-ecgonine methyl ester, however, has an absolute configuration different from that of anhydro-ecgonine methyl ester derived from natural (−)-cocaine.

DISCLOSURE OF THE INVENTION

In view of such conditions, the present invention is intended to provide a process for producing an optically active tropinonemonocarboxylic acid ester derivative useful as an intermediate for synthesizing an optically active tropane derivative without using cocaine as a starting material.

The present invention relates to a process for producing an optically active tropinonemonocarboxylic acid ester derivative which comprises subjecting a tropinonedicarboxylic acid ester derivative represented by the following formula (1):

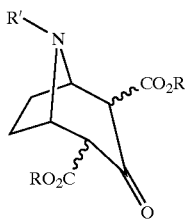

(1)

wherein R' is an alkyl group, an aralkyl group or an amino-protecting group selected from lower aliphatic acyl groups, aromatic acyl groups, lower alkoxycarbonyl groups, aralkyloxycarbonyl groups, aryloxycarbonyl groups and tri-lower-alkylsilyl groups, and R is an alkyl group or an aralkyl group, to asymmetric dealkoxycarbonylation in the presence of an enzyme to obtain an optically active tropinonemonocarboxylic acid ester derivative represented by the following formula (2):

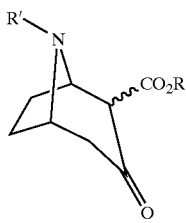

(2)

wherein R and R' are as defined above.

The present invention also relates to a process for producing an optically active tropinonemonocarboxylic acid ester derivative which comprises reacting succindi-aldehyde represented by the following formula (3):

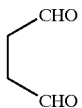

(3)

with an organic amine represented by the following formula (4):

R''—NH$_2$ (4)

wherein R'' is an alkyl group or an aralkyl group, and an acetonedicarboxylic acid ester represented by the following formula (5):

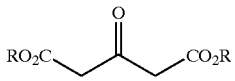

(5)

wherein R is an alkyl group or an aralkyl group; if necessary, converting the substituent derived from the substituent R'' of the organic amine of the formula (4) to an amino-protecting group; thereby obtaining a tropinonedicarboxylic acid ester derivative represented by the following formula (1):

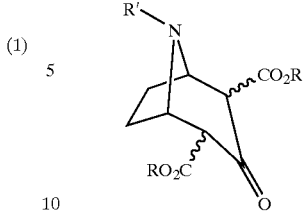

(1)

wherein R' is an alkyl group, an aralkyl group or an amino-protecting group selected from lower aliphatic acyl groups, aromatic acyl groups, lower alkoxycarbonyl groups, aralkyloxycarbonyl groups, aryloxycarbonyl groups and tri-lower-alkylsilyl groups, and R is an alkyl group or an aralkyl group; and then subjecting the tropinonedicarboxylic acid ester derivative to asymmetric dealkoxycarbonylation in the presence of an enzyme to obtain an optically active tropinonemonocarboxylic acid ester derivative represented by the following formula (2):

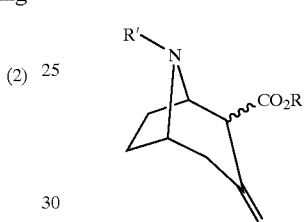

(2)

wherein R and R' are as defined above.

The present invention further relates to a process for producing an optically active anhydroecgonine carboxylic acid ester derivative which comprises converting the substituent R' and/or substituent R of the optically active tropinonemonocarboxylic acid ester derivative of the above formula (2) to another substitu-ent or other substituents if necessary, reducing the oxo group at the 3-position of this derivative, and then dehydrating the resulting compound to obtain an optically active anhydroecgonine carboxylic acid ester derivative represented by the following formula (6):

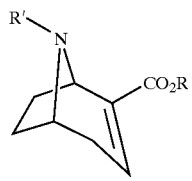

(6)

wherein R and R' are as defined above.

BEST MODE FOR CARRYING OUT THE INVENTION

The optically active tropinonemonocarboxylic acid ester derivative obtained by the production process of the present invention is useful as an intermediate for synthesizing a cocaine analogue without using cocaine as a starting material, said cocaine analogue having a tropane skeleton, the basic ring structure of cocaine, and having the same optical activity as that of a cocaine analogue derived from natural (−)-cocaine.

The tropinonedicarboxylic acid ester derivative of the above formula (1), the starting material in the production process of the present invention, may be synthesized by the process shown in the following reaction scheme B:

Reaction scheme B

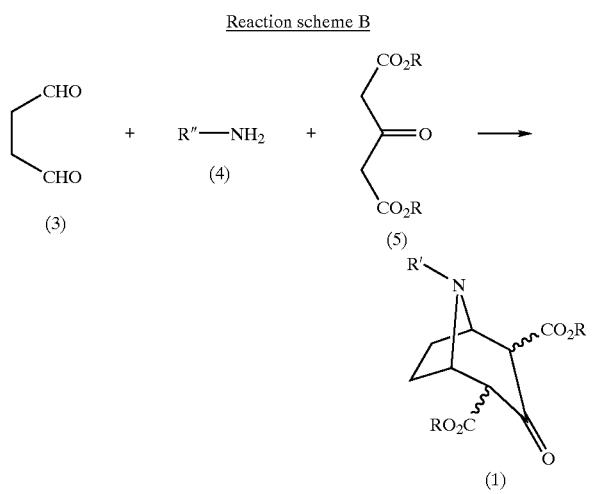

As shown in the reaction scheme B, the tropinonedicarboxylic acid ester derivative of the formula (1) is synthesized by reacting succindialdehyde of the formula (3) with an organic amine of the formula (4) and an acetonedicarboxylic acid ester of the formula (5) and, if necessary, converting the substituent derived from the substituent R" of the organic amine of the formula (4) to an amino-protecting group.

Succindialdehyde of the formula (3) is a well-known compound and is obtained, for example, by hydrolyzing 2,5-dimethoxytetrahydrofuran.

The organic amine of the formula (4) and the acetonedicarboxylic acid ester of the formula (5) are also well-known compounds and are synthesized by per se well-known processes. Each of the substituent R" of the organic amine of the formula (4) and the substituent R of the acetonedicarboxylic acid ester of the formula (5) is an alkyl group or an aralkyl group. Specific examples of the alkyl group are alkyl groups of 1 to 6 carbon atoms, such as methyl group, ethyl group, propyl group, isopropyl group, butyl group, s-butyl group, t-butyl group, pentyl group, isopentyl group, neopentyl group, t-pentyl group, hexyl group, etc. Specific examples of the aralkyl group are aralkyl groups of 7 to 10 carbon atoms, such as benzyl group, phenethyl group, phenylpropyl group, phenylbutyl group, etc.

The reaction of succindialdehyde of the formula (3) with the organic amine of the formula (4) and the acetonedicarboxylic acid ester of the formula (5) is per se well known. For example, when each of the substitu-ents R and R" is a methyl group (Me), a methanolic solution containing dimethyl 1,3-acetonedicarboxylate is added to a methanol solution of succindialdehyde in an ice bath under a nitrogen atmosphere, a methanolic solution containing methylamine is added dropwise thereto in an ice bath and stirred overnight, and the solvent is distilled off to obtain dimethyl 8-methyl-3-oxo-8-azabicyclo[3.2.1]octane-2,4-dicarboxylate (1a: R'=Me and R=Me in the formula (1)) in a yield of 70–90 mol %.

The thus obtained tropinonedicarboxylic acid ester derivative may be subjected as it is to the asymmetric dealkoxycarbonylation explained hereinafter. If necessary, the alkyl or aralkyl group as the substituent R' of the amino group at the 8-position derived from the substituent R" of the organic amine of the formula (4) may be converted to an amino-protecting group. The amino-protecting group includes lower aliphatic acyl groups, aromatic acyl groups, lower alkoxycarbonyl groups, aralkyloxycarbonyl groups, aryloxycarbonyl groups and tri-lower-alkylsilyl groups, etc. As the lower aliphatic acyl groups, there may be exemplified lower aliphatic acyl groups of 2 to 7 carbon atoms, such as acetyl group, propanoyl group, butanoyl group, pentanoyl group, hexanoyl group, etc. As the aromatic acyl groups, there may be exemplified aromatic acyl groups of 7 to 11 carbon atoms, such as benzoyl group, naphthanoyl group, etc. As the lower alkoxy-carbonyl groups, there may be exemplified lower alkoxycarbonyl groups of 2 to 7 carbon atoms, such as methoxycarbonyl group, ethoxycarbonyl group, butoxycarbonyl group, t-butoxycarbonyl group, etc. As the aralkyloxycarbonyl groups, there may be exemplified aralkyloxycarbonyl groups of 8 or 9 carbon atoms, such as benzyloxycarbonyl group, methoxybenzyloxycarbonyl group, etc. As the aryloxycarbonyl groups, there may be exemplified aryloxycarbonyl groups of 7 to 11 carbon atoms, such as phenoxycarbonyl group, naphthoxycarbonyl group, etc. As the tri-lower-alkylsilyl groups, there may be exemplified tri($C_1$–$C_6$)alkylsilyl groups such as trimethylsilyl group, triethylsilyl group, tributylsilyl group, etc.

The conversion to any of these amino-protecting groups is a per se well-known reaction.

A desired optically active tropinonemonocarboxylic acid ester derivative of the formula (2) is obtained by subjecting the thus obtained tropinonedicarboxylic acid ester derivative of the formula (1) to asymmetric dealkoxycarbonylation using an enzyme, as shown in the following reaction scheme C:

Reaction scheme C

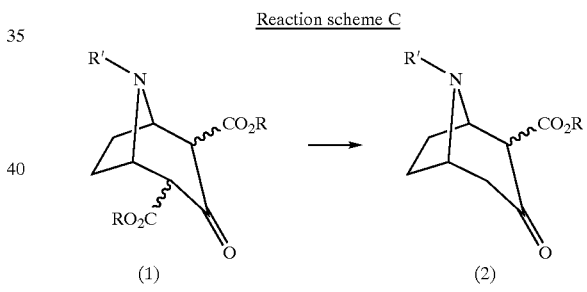

In this case, the optically active tropinonemonocarboxylic acid ester derivative of the formula (2) obtained by enzyme-catalyzed asymmetric dealkoxycarbonylation of the ester group at the 2- or 4-position of the tropinonedicarboxylic acid ester derivative of the formula (1) is effectively used as an intermediate for synthesis of various cocaine analogues.

The yield of the optically active tropinonemonocarboxylic acid ester derivative of the formula (2) from the asymmetric dealkoxycarbonylation of the tropinonedicarboxylic acid ester derivative of the formula (1) and its optical purity are affected by the kinds of the substituent R' of the amino group at the 8-position, the substituent R of the ester group at the 2- or 4-position and the enzyme used. In particular, the kinds of the substituent of the ester group and the enzyme used have a great influence.

As the enzyme used in the present invention, there may be exemplified liver esterases such as porcine liver esterase (PLE), rabbit liver esterase, horse liver esterase, etc.; and baker's yeast (B.Y.). In particular, porcine liver esterase (PLE) and baker's yeast (B.Y.) are suitably used.

A preferable combination of the substituent R' of the amino group at the 8-position and the substituent R of the ester group at the 2- or 4-position of the tropinonedicarboxylic acid ester derivative of the formula (1) is a combination wherein R is an alkyl group of 1 to 6 carbon atoms and R' is an aralkyl group, a lower aliphatic acyl group, an aromatic acyl group, an aryloxycarbonyl group or a tri-lower-alkylsilyl group; a combination wherein R is an alkyl group of 2 to 6 carbon atoms and R' is an aralkyloxycarbonyl group; or a combination wherein each of R and R' is an aralkyl group. More specifically, preferable is a combination wherein R is an alkyl group of 1 to 6 carbon atoms selected from methyl group, ethyl group, propyl group, isopropyl group, butyl group, isobutyl group, s-butyl group, t-butyl group, pentyl group, isopentyl group, neopentyl group, t-pentyl group and hexyl group, and R' is an aralkyl group of 7 to 10 carbon atoms selected from benzyl group, phenethyl group, phenylpropyl group and phenylbutyl group; a combination wherein R is an alkyl group of 2 to 6 carbon atoms selected from ethyl group, propyl group, isopropyl group, butyl group, isobutyl group, s-butyl group, t-butyl group, pentyl group, isopentyl group, neopentyl group, t-pentyl group and hexyl group, and R' is an aralkyloxycarbonyl group of 8 or 9 carbon atoms selected from benzyloxycarbonyl group and methoxybenzyl-oxycarbonyl group; or a combination wherein each of R and R' is an aralkyl group of 7 to 10 carbon atoms selected from benzyl group, phenethyl group, phenylpropyl group and phenylbutyl group.

Preferable examples of the tropinonedicarboxylic acid ester derivative of the formula (1) which have any of these combinations are the following compounds:

dimethyl 8-benzyl-3-oxo-8-azabicyclo[3.2.1]-octane-2,4-dicarboxylate (1b: R'=Bn and R=Me in the formula (1)), diethyl 8-benzyl-3-oxo-8-azabicyclo[3.2.1]-octane-2,4-dicarboxylate (1c: R'=Bn and R=Et in the formula (1)), diisopropyl 8-benzyl-3-oxo-8-azabicyclo[3.2.1]-octane-2,4-dicarboxylate (1d: R'=Bn and R=i-Pr in the formula (1)), dibutyl 8-benzyl-3-oxo-8-azabicyclo[3.2.1]-octane-2,4-dicarboxylate (1e: R'=Bn and R=n-Bu in the formula (1)), dibenzyl 8-benzyl-3-oxo-8-azabicyclo[3.2.1]-octane-2,4-dicarboxylate (1f: R'=Bn and R=Bn in the formula (1)), and diethyl 8-benzyloxycarbonyl-3-oxo-8-azabicyclo[3.2.1]octane-2,4-dicarboxylate (1g: R'=Z and R=Et in the formula (1)).

The asymmetric dealkoxycarbonylation is carried out at pH 7–9 and at a temperature of approximately 10–40° C. As a buffer solution, there are used phosphate buffer solutions, toluene-phosphate buffer solutions, Tris buffer solutions, HEPES buffer solutions, etc. The amount of the enzyme used is varied depending on the kind of the enzyme. For example, the amount of PLE is 500–5,000 units/mmol substrate, and the amount of B.Y. is 1–5 g/mmol substrate.

The optically active tropinonemonocarboxylic acid ester derivative of the formula (2) is obtained by the asymmetric dealkoxycarbonylation. When the compounds described above as preferable examples of the tropinone-dicarboxylic acid ester derivative of the formula (1) are used, the following corresponding compounds of the formula (2) are obtained:

methyl (1R,5S)-8-benzyl-3-oxo-8-azabicyclo[3.2.1]octane-2-carboxylate ((−)-2b: R'=Bn and R=Me in the formula (2)), ethyl (1R,5S)-8-benzyl-3-oxo-8-azabicyclo[3.2.1]octane-2-carboxylate ((−)-2c: R'=Bn and R=Et in the formula (2)), isopropyl (1R,5S)-8-benzyl-3-oxo-8-azabicyclo[3.2.1]octane-2-carboxylate ((−)-2d: R'=Bn and R=i-Pr in the formula (2)), butyl (1R,5S)-8-benzyl-3-oxo-8-azabicyclo[3.2.1]octane-2-carboxylate ((−)-2e: R'=Bn and R=n-Bu in the formula (2)), benzyl (1R,5S)-8-benzyl-3-oxo-8-azabicyclo[3.2.1]octane-2-carboxylate ((−)-2f: R'=Bn and R=Bn in the formula (2)), and ethyl (1R,5S)-8-benzyloxycarbonyl-3-oxo-8-azabicyclo[3.2.1]octane-2-carboxylate ((−)-2g: R'=Z and R=Et in the formula (2)).

The optically active tropinonemonocarboxylic acid ester derivative obtained according to the present invention is a mixture of three kinds of isomers, i.e., enol form and two keto forms as shown in the following reaction scheme D. This fact can be confirmed by NMR data of the derivative.

Reaction scheme D

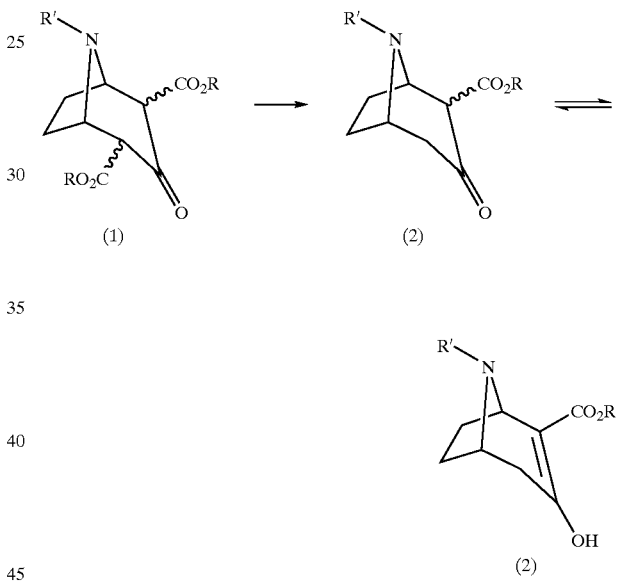

Therefore, the optical purity of the optically active tropinonemonocarboxylic acid ester derivative obtained according to the present invention was measured by converting said derivative to an α,β-unsaturated ester compound, a single compound by reduction and dehydration as shown in the following reaction scheme E, and then subjecting this ester compound to HPLC using a chiral column:

Reaction scheme E

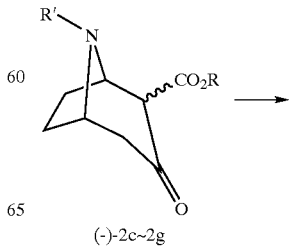

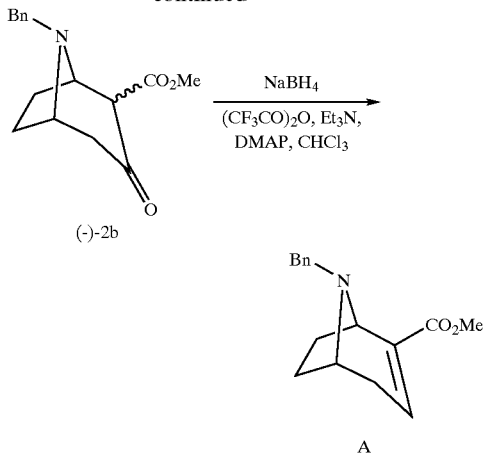

Specifically, for example, each of the above-exemplified compounds (−)-2c, (−)-2d, (−)-2e and (−)-2f, i.e., optically active tropinonemonocarboxylic acid ester derivatives obtained according to the present invention is converted to the above-exemplified compound (−)-2b, a methyl ester compound by transesterification, which is then converted to the α,β-unsaturated ester compound A by reduction and dehydration, and the compound A is subjected to HPLC using a chiral column (eluent: hexane:2-propanol=100:1), whereby the optical purity was measured. The optical purity of the above-exemplified compound (−)-2g having a benzyloxycarbonyl group as a protecting group for the amino group may be measured by removing the benzyloxycarbonyl group with trifluoroacetic acid (TFA), benzylating the resulting compound into the above-exemplified compound (−)-2c, and then converting the compound (−)-2c to the a unsaturated ester compound A in the manner shown in the reaction scheme E.

α,β-Unsaturated ester compound A in dl-form used as a reference standard compound was synthesized by hydrolyzing dimethyl 8-benzyl-3-oxo-8-azabicyclo[3.2.1]-octane-2,4-dicarboxylate (1b: R'=Bn and R=Me in the formula (1)) with LiOH, decarboxylating the hydrolysate into tropinonemonoester with 2N-HCl, and reducing this compound with NaBH$_4$, followed by dehydration.

As to the absolute configuration, as shown in the following reaction scheme F, each of the above-exemplified compounds (−)-2c, (−)-2d, (−)-2e, (−)-2f and (−)-2g, i.e., the optically active tropinonemonocarboxylic acid ester derivatives obtained according to the present invention, is converted to methyl 8-methyl-3-oxo-8-azabicyclo[3.2.1]octane-2-carboxylate ((+)-B), and this compound is reduced and then dehydrated to obtain anhydroecgonine methyl ester ((−)-C). On the other hand, as shown in the following reaction scheme G, natural (−)-cocaine was converted to anhydroecgonine methyl ester. When the anhydroecgonine methyl ester obtained from each of the above-exemplified compounds was compared with that obtained from natural (−)-cocaine, their directions of optical rotation were the same (−) in the case of all the above-exemplified ompounds. It was confirmed by this fact that the absolute configuration of the optically active tropinonemonocarboxylic acid ester derivative obtained by the enzyme reaction according to the present invention is identical to that of (−)-cocaine.

Reaction scheme F

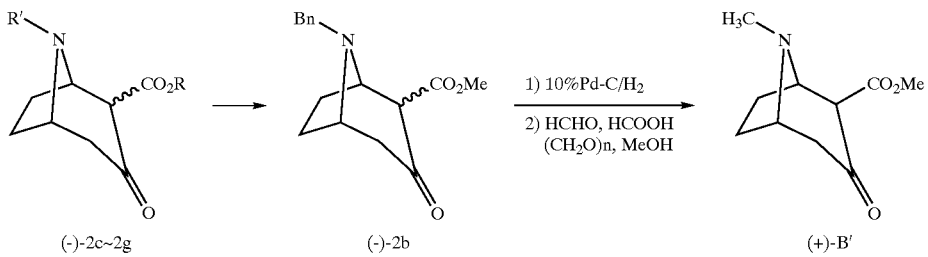

Reaction scheme G

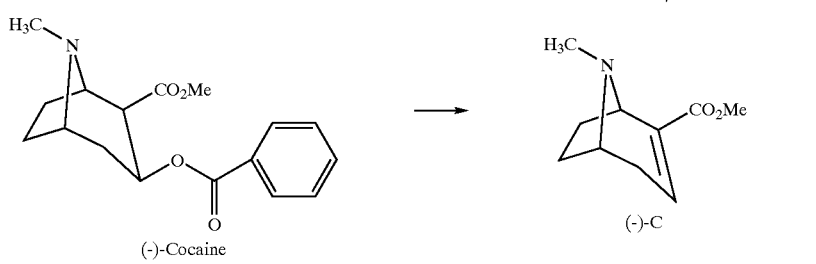

The thus obtained optically active tropinonemonocarboxylic acid ester derivative according to the present invention may be converted to an optically active anhydroecgonine carboxylic acid ester derivative represented by the following formula (6):

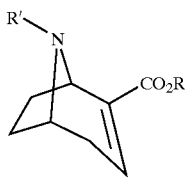

(6)

wherein R and R' are as defined above, by converting the substituent R' and/or the substituent R to another substituent or other substituents if necessary, and then reducing the oxo group at the 3-position, followed by dehydration. Such an optically active anhydroecgonine carboxylic acid ester derivative is useful as an intermediate for synthesis of drugs such as 2β-carbomethoxy-3β-(4-iodophenyl)tropane (β-CIT) and its derivatives including β-CIT-FP and tropane alkaloids such as (−)-ferruginine.

(+)-Ferruginine is an alkaloid isolated from Darlingiana ferruginea and D. darlingiana, and its enantiomer (−)-ferruginine is known as an agonist for nicotine-like acetylcholine receptors. The (+)-form and (−)-form of ferruginine have been synthesized from L-glutamic acid (H. Rapoport et al., J. Org. Chem. 1996, 61, 314).

For example, using butyl (1R,5S)-8-benzyl-3-oxo-8-azabicyclo[3.2.1]octane-2-carboxylate ((−)-2e: R'=Bn and R=n-Bu in the formula (2)), an optically active tropinonemonocarboxylic acid ester derivative obtained according to the present invention, (−)-ferruginine may be synthesized as shown in the=Boc and R=Me in the formula (6)), an optically active anhydroecgonine carboxylic acid ester derivative. The methyl ester group and Boc group of the optically active anhydroecgonine carboxylic acid ester derivative obtained are replaced by an acetyl group and a methyl group, respectively, by well-known methods to obtain a desired compound (−)-ferruginine.

Physiological properties such as optical rotation, $^1$H-NMR, etc. of the optically active anhydroecgonine carboxylic acid ester derivative obtained above, i.e., methyl (1R,5S)-8-t-butoxycarbonyl-8-azabicyclo[3.2.1]octan-2-ene-2-carboxylate ((−)-6a), agree with the values described in a reference (H. Rapoport et al., J. Org. Chem. 1996, 61, 314). Thus, the synthesis of (−)-ferruginine has been achieved.

As shown in the following reaction scheme I, each of the drug 2β-carbomethoxy-3β-(4-iodophenyl)-tropane (β-CIT) and its derivative β-CIT-FP may be synthesized from methyl (1R,5S)-8-benzyl-3-oxo-8-azabicyclo[3.2.1]octane-2-carboxylate ((−)-2b: R'=Bn and R=Me in the formula (2)), an optically active tropinonemonocarboxylic acid methyl ester obtained according to the present invention. following reaction scheme H.

Reaction scheme H

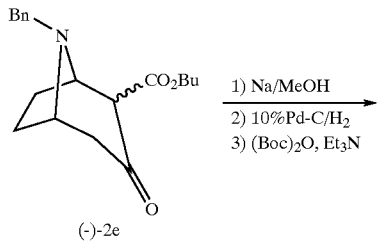

At first, butyl (1R,5S)-8-benzyl-3-oxo-8-azabicyclo[3.2.1]octane-2-carboxylate ((−)-2e) is converted to methyl (1R,5S)-8-benzyl-3-oxo-8-azabicyclo[3.2.1]octane-2-carboxylate ((−)-2b: R'=Bn and R=Me in the formula (2)) by transesterification, and then the benzyl group as a protecting group for the amino group is removed by catalytic reduction and a t-butoxycarbonyl (Boc) group is introduced. The resulting keto-ester, methyl (1R,5S)-8-t-butoxycarbonyl-3-oxo-8-azabicyclo[3.2.1]octane-2-carboxylate ((−)-2h: R'=Boc and R=Me in the formula (2)) is reduced with NaBH$_4$ and then dehydrated to obtain methyl (1R,5S)-8-t-butoxycarbonyl-8-azabicyclo[3.2.1]octan-2-ene-2-carboxylate ((−)-6a: R'

Reaction scheme I

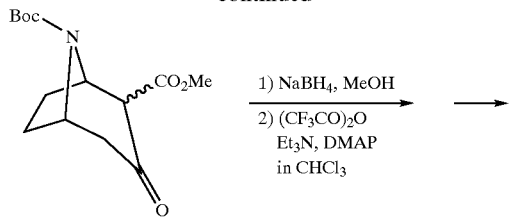

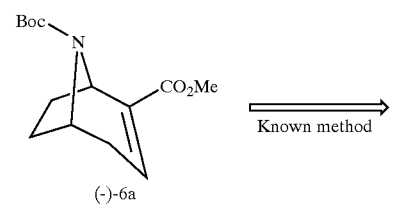

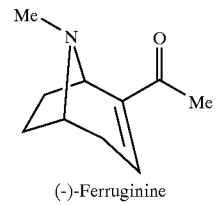

(−)-Ferruginine

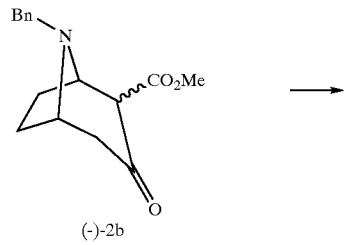

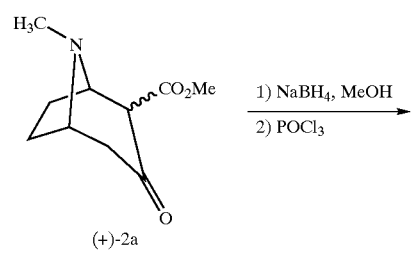

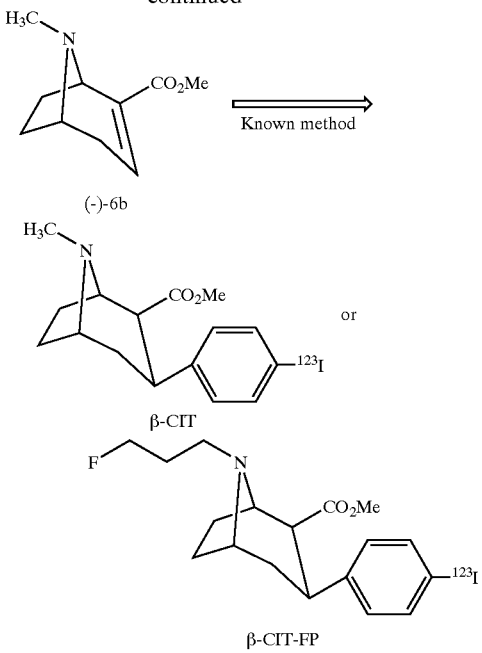

In detail, the benzyl group of methyl (1R,5S)-8-benzyl-3-oxo-8-azabicyclo[3.2.1]octane-2-carboxylate ((−)-2b) is replaced by a methyl group to obtain methyl (1R,5S)-8-methyl-3-oxo-8-azabicyclo[3.2.1]octane-2-carboxylate ((+)-2a: R'=Me and R=Me in the formula (2)). Thereafter, the obtained compound may be converted to methyl (1R,5S)-8-methyl-8-azabicyclo[3.2.1]octan-2-ene-2-carboxylate ((−)-6b: R'=Me and R=Me in the formula (6)), optically active anhydroecgonine methyl ester by reduction with NaBH$_4$ followed by dehydration. From this optically active anhydroecgonine methyl ester, β-CIT or β-CIT-FP may be synthesized according to a well-known process.

As exemplified above, the optically active tropinonemonocarboxylic acid ester derivative of the formula (2) obtained by the process of the present invention may be converted to an optically active anhydroecgonine carboxylic acid ester derivative of the formula (6) which is useful as an intermediate for synthesis of drugs, by converting the substituent R' and/or the substituent R to another substituent or other substituents if necessary, and then reducing the oxo group at the 3-position, followed by dehydration. In this case, the conversion of the substituent R' and/or the substituent R to another substituent or other substituents may be carried out by a well-known reaction such as transesterification as is clear from the example described above. The reduction and dehydration are per se well-known reactions. For example, the reduction may be carried out with NaBH$_4$ or PtO$_2$, and the dehydration may be carried out with trifluoroacetic anhydride (TFAA), POCl$_3$ or the like.

The anhydroecgonine carboxylic acid ester derivative obtained according to the present invention is optically active and is very useful as an intermediate for synthesis of drugs.

In general, the optical purity of an optically active substance used as a drug is very important in imparting a specific pharmacological effect and preventing side effects, etc. Easy production of an optically active tropinonemonocarboxylic acid ester derivative having a high optical purity has been successfully achieved by carrying out the asymmetric dealkoxycarbonylation of a tropinonedicarboxylic acid ester derivative according to the present invention. In addition, it has become possible to obtain easily an anhydroecgonine ester derivative having a very high optical purity by synthesizing an anhydroecgonine carboxylic acid ester derivative by the use of the optically active tropinonemonocarboxylic acid ester derivative having a high optical purity. Moreover, it is possible to synthesize a crystalline anhydroecgonine ester derivative. Furthermore, it has become possible to produce easily a crystalline anhydroecgonine ester derivative having a much higher optical purity by purification by recrystallization.

For example, when as shown in the following reaction scheme J, methyl (1R,5S)-8-t-butoxycarbonyl-8-azabicyclo[3.2.1]octan-2-ene-2-carboxylate ((−)-6a: R'=Boc and R=Me in the formula (6)) was synthesized by converting the substituent of the amino group of methyl (1R,5S)-8-benzyl-3-oxo-8-azabicyclo[3.2.1]octane-2-carboxylate ((−)-2b: R'=Bn and R=Me in the formula (2)) to a Boc group, and reducing the resulting compound, followed by dehydration, colorless needles (mp 79–80° C.) were obtained. Thus, it has become very easy to increase the optical purity by recrystallization. Crystalline methyl (1R,5S)-8-methyl-8-azabicyclo[3.2.1]octan-2-ene-2-carboxylate ((−)-6b: R'=Me and R=Me in the formula (6)) having a very high optical purity may be synthesized by replacing the Boc group of the compound (−)-6a by a methyl group.

Reaction scheme J

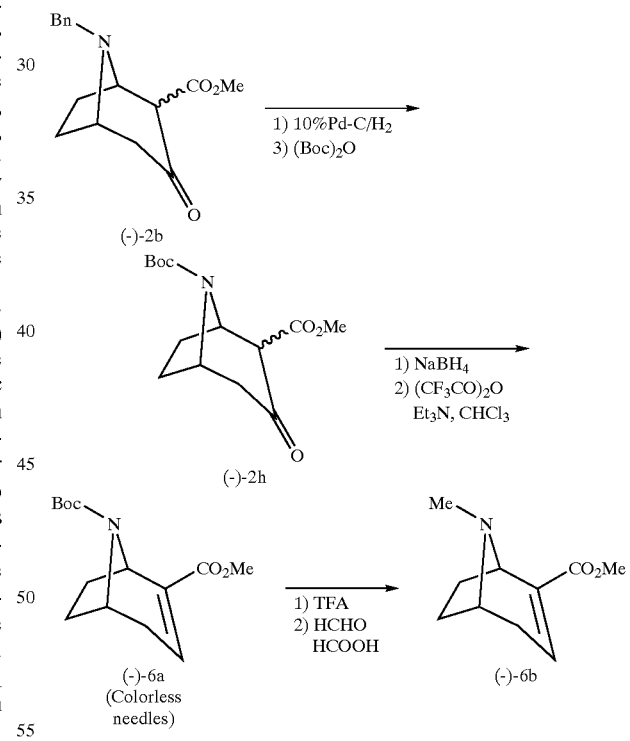

The present invention is illustrated in further detail with the following examples, which should not be construed as limiting the scope of the invention.

Methods for measuring physical properties of substances obtained, common solvents, etc. are as follows.

(1) Melting point: Measured by using a micro hot-stage apparatus (Yanagimoto) and a directly heated capillary melting point apparatus (Mitamura Riken Industries, Ltd.).

(2) $^1$H-NMR: Measured with a Varian XL-300 spectrometer. Chemical shift values are expressed in ppm by using tetramethylsilane (TMS) as an internal standard.

(3) Optical rotation: Measured with Horiba Sepa-200.

(4) Infrared spectrum: Measured with Jasco IR-810 and SHIMADZU FTIR-8300. Frequencies are expressed in cm$^{-1}$.

(5) Mass spectrum: Measured with a JEOL AJMX-SX102AQQ mass spectrometer and a JEOL JMS-GCmate mass spectrometer.

(6) Elemental analysis: Measured with PERKINELMER Series CHNS/O Analyzer 2400.

(7) Silica gel for chromatography: Wakogel C-200 (Wako Pure Chemical Industries, Ltd.), Silica Gel 60 $PF_{254}$ (Nacalai Tesque, Inc.), Kieselgel 60 Art. 9385 (Merck), TLC-Kieselgel 60 Art. 11695 (Merck), Silica Gel 60 N (Kanto Chemical Co., Inc.) and SIL-60-S75 (YMC CO., LTD.) were used.

(8) Silica gel plates for preparative-TLC: Kieselgel 60 $F_{254}$Art. 5715 (Merck, 0.25 mm) and Kieselgel 60 $F_{254}$Art. 5744 (Merck, 0.5 mm) were used.

(9) Preparative-HPLC: JAI LC-908 was used. As columns, JAIGEL-1H, JAIGEL-2H and JAIGEL-SIL S-043-15 were used.

(10) HPLC for qualitative analysis: Shimadzu LC-10A was used. As a column, Daicel Chiral Column (CHIRALCEL OD) was used.

(11) Solvents: As an ether solvent or aromatic solvent used in each reaction, there was used one which had been made anhydrous by distilling from sodium benzophenone ketyl at the time of use. As chloroform, there was used one which had been mede anhydrous by distilling from $CaCl_2$, after ten washings with water to remove a stabilizer ethanol at the time of use. As other anhydrous solvents, there were used those which had been made anhydrous according to a conventional method.

(12) The following abbreviations are used in the examples described below:

Ac: acetyl group, Bn; benzyl group, Bu; butyl group, Boc: t-butoxycarbonyl group, Z; benzyloxycarbonyl group, DMAP; 4-dimethylaminopyridine, $Et_3N$; triethylamine, MeOH; methanol, THF; tetrahydrofuran, AcOEt; ethyl acetate, PLE; porcine liver esterase, PPL; porcine pancreas lipase, B.Y.; baker's yeast, MS4A; molecular sieve 4A.

EXAMPLE 1

Synthesis of Dimethyl 8-Methyl-3-oxo-8-azabicyclo [3.2.1]octane-2,4-dicarboxylate (1a: R'=Me and R= Me in the Formula (1))

To an aqueous solution (30 ml) of of 2,5-dimethoxytetrahydrofuran (6.48 ml, 50 mmol) was added concentrated hydrochloric acid (6 ml), and the resulting mixture was stirred at room temperature for 3 hours. After completion of the reaction, the reaction solution was neutralized with potassium carbonate and the excess methanol was evapolated under reduced pressure. The residue was extracted by using an Extrelut colomn, a colomn for extraction, with chloroform. The extract was dried over MS4A and magnesium sulfate, filtered and concentrated in vacuo, whereby a crude product of succindialdehyde was obtained.

Under a nitrogen atmosphere, to the obtained succindialdehyde were added droupwise a methanol (70 ml) solution of dimethyl 1,3-acetonedicarboxylate (7.49 ml, 70 mmol) and a methanol (30 ml) solution of methylamine (7.15 ml, 70 mmol) at 0° C. and the mixture was stirred overnight. After completion of the reaction, the solvent was evapolated under reduced pressure and the thus obtained crude product was purified by a silica gel column chromatography ($CHCl_3$:MeOH=100:1) to obtain 11.9 g of the title compound dimethyl 8-methyl-3-oxo-8-azabicyclo[3.2.1]octane-2,4-dicarboxylate. The yield was 91 mol %. Light-yellow oil (a mixture of tautomers and concurrently stereoisomers); $^1$H-NMR ($CDCl_3$, 300 MHz): δ 11.9 (s, 0.43H), 11.8 (s, 0.43H), 4.01–3.47 (m, 8H), 3.18 (d, J=2.4 Hz, 0.38H), 2.98 (d, J=1.2 Hz, 0.76H), 2.39 (s, 1.29H), 2.30 (s, 1.71H), 2.27–1.51 (m, 4H); IR ($CHCl_3$): 3689, 1735, 1654, 1622, 1444, 1249, 1244, 1174 cm$^{-1}$; MS(FAB) m/z 356 ($M^+$+H, 100), HRMS(FAB) $C_{12}H_{18}NO_5$ ($M^+$+H): Calcd. 256.1185, Found 256.1179.

EXAMPLE 2

Synthesis of Dimethyl 8-Benzyl-3-oxo-8-azabicyclo [3.2.1]octane-2,4-dicarboxylate (1b: R'=Bn and R= Me in the Formula (1))

Under a nitrogen atmosphere, a methanol (15 ml) solution of benzylamine (5.46 ml, 50 mmol) was added dropwise to a methanol (15 ml) solution of succindialdehyde obtained in the same manner as in Example 1, at 0° C. and stirred for 2 hours. Then, a methanol (15 ml) solution of dimethyl 1,3-acetonedicarboxylate (7.22 ml, 50 mmol) was added dropwise at 0° C. and the reaction mixture was stirred for an additional 19 hours.

After completion of the reaction, the solvent was evapolated undder reduced pressure and the thus obtained crude product was purified by a silica gel column chromatography (AcOEt:hexane=1:5) to obtain 11.8 g of the title compound dimethyl 8-benzyl-3-oxo-8-azabicyclo[3.2.1]-octane-2,4-dicarboxylate. The yield was 74 mol %.

Light-yellow oil (a mixture of tautomers and concurrently stereoisomers); $^1$H-NMR ($CDCl_3$, 300 MHz): δ 11.9 (s, 0.25H), 11.8 (s, 0.25H), 7.34–7.24 (m, 5H), 4.09–3.82 (m, 1H), 3.78–3.57 (m, 9H), 3.37 (s, 0.33H), 3.33 (s, 0.33H), 3.18 (d, J=2.4 Hz, 0.33H), 2.96 (d, J=1.5 Hz, 0.5H), 2.25–1.49 (m, 4H); IR ($CHCl_3$): 3690, 1738, 1659, 1620, 1603, 1445, 1263, 1236 cm$^{-1}$; MS(FAB) m/z 332 ($M^+$+H, 100); HRMS(FAB) $C_{18}H_{22}NO_5$ ($M^+$+H): Calcd. 332.1498, Found 332.1493.

EXAMPLE 3

Synthesis of Dimethyl 8-Benzyloxycarbonyl-3-oxo-8-azabicyclo[3.2.1]octane-2,4-dicarboxylate (1h: R'=Me and R=Z in the Formula (1))

To a solution in acetic acid (50 ml) of the dimethyl 8-benzyl-3-oxo-8-azabicyclo[3.2.1]octane-2,4-dicarboxylate obtained in Example 2 was added 10% Pd-C (catalytic amount), and the resulting mixture was stirred for 9 hours under a hydrogen atmosphere at 40° C. After completion of the reaction, the mixture was filtered with Celite and concentrated in vacuo. The residue was adjusted to pH 8.0–8.5 with a saturated sodium carbonate solution and extracted with chloroform. The extract was dried over $Na_2SO_4$, filtered and concentrated in vacuo, whereby a crude product of a debenzylated derivative dimethyl 3-oxo-8-azabicyclo[3.2.1]octane-2,4-dicarboxylate was obtained. To a solution of the obtained debenzylated derivative in chloroform (80 ml) were added benzyloxycarbonyl chloride (1.80 ml, 12.6 mmol) and triethylamine (1.76 ml, 12.6 mmol), and the resulting mixture was stirred under a nitrogen atmosphere at room temperature for 11 hours. After completion of the reaction, a saturated aqueous sodium chloride solution was added to the reaction mixture, and then extracted with chloroform. The extract was dried over $Na_2SO_4$, filtered and concentrated in vacuo, and the thus obtained crude product was purified by a silica gel column chromatography (AcOEt:hexane=1:2) to obtain 2.75 g of the title compound dimethyl 8-benzyloxycarbonyl-3-oxo-8-azabicyclo[3.2.1]octane-2,4-dicarboxylate. The yield from the above two steps was 87 mol %. Light-yellow oil (a mixture of tautomers and concurrently stereoisomers); $^1$H-NMR (CDCl$_3$, 300 MHz): δ 11.7 (s, 0.25H), 7.40–7.30 (m, 5H), 5.23–4.70 (m, 4H), 3.82–3.59 (m, 6H), 3.44 (s, 1H), 3.10 (s, 0.25H), 3.09 (s, 0.5H), 2.40–1.56 (m, 4H); IR (CHCl$_3$): 1739, 1701, 1662, 1618, 1498, 1444, 1436, 1425, 1369, 1336, 1319, 1303, 1290, 1265, 1244 cm$^{-1}$; MS(FAB) m/z 376 (M$^+$+H, 57); HRMS(FAB) $C_{19}H_{22}NO_7$ (M$^+$+H): Calcd. 376.1397, Found 376.1395.

EXAMPLE 4

Synthesis of Dimethyl 8-t-Butoxycarbonyl-3-oxo-8-azabicyclo[3.2.1]octane-2,4-dicarboxylate (1i: R'= Boc and R=Me in the Formula (1))

To a solution in chloroform (30 ml) of the debenzylated derivative dimethyl 3-oxo-8-azabicyclo[3.2.1]octane-2,4-dicarboxylate (1.37 g, 5.62 mmol) obtained in Example 3 were added di-t-butyl dicarbonate (1.55 ml, 6.75 mmol) and triethylamine (0.94 ml, 6.75 mmol), and the resulting mixture was stirred under a nitrogen atmospere at room temperature. After completion of the reaction, a saturated aqueous sodium chloride solution was added to the reaction mixture, and then extracted with chloroform. The extract was dried over $Na_2SO_4$, filtered and then concentrated in vacuo, and the thus obtained crude product was purified by a silica gel column chromatography (AcOEt:hexane=1:5) to obtain 1.90 g of the title compound dimethyl 8-t-butoxycarbonyl-3-oxo-8-azabicyclo[3,2,1]-octane-2,4-dicarboxylate. The yield was 98 mol %.

Colorless needles (a mixture of tautomers and concurrently stereoisomers); mp 89–90° C. (AcOEt/hexane=1/4); $^1$H-NMR (CDCl$_3$, 300 MHz): δ 11.9 (s, 0.2H), 11.8 (s, 0.3H), 5.03–4.58 (m br, 1.8H), 4.16 (d, J=3.7 Hz, 0.2H), 3.82–3.66 (m, 6H), 3.49 (s, 0.25H), 3.33 (s, 0.25H), 3.07 (s, 0.5H), 2.31–1.78 (m, 2.5H), 1.69–1.59 (m, 1H), 1.54–1.22 (m, 10H); IR (KBr): 1743, 1693, 1654, 1622, 1439, 1417, 1390, 1367, 1336, 1298, 1276, 1224, 1207, 1161, 1105, 1049, 1020 cm$^{-1}$; MS(FAB) m/z 342 (M$^+$+H, 44); HRMS (FAB) $C_{16}H_{24}NO_7$ (M$^+$+H): Calcd. 342.1553, Found 342.1555; Elemental analysis Calcd. $C_{16}H_{23}NO_7$: C, 56.30; H, 6.79; N, 4.10. Found: C, 56.38; H, 6.94; N, 4.08.

EXAMPLE 5

Synthesis of Methyl 8-Methyl-3-oxo-8-azabicyclo [3.2.1]octane-2-carboxylate (2a: R'=Me and R=Me in the Formula (2))

Lipase PS (3.79 g) was added to a mixture of the dimethyl 8-methyl-3-oxo-8-azabicyclo[3.2.1]octane-2,4-dicarboxylate (1a) (430 mg, 1.68 mmol) of obtained in Example 1, toluene (10 ml) and 0.3 M phosphate buffer (pH=7.2, 10 ml), and the resulting mixture was stirred at room temperature for 3 days. After completion of the reaction, the reaction mixture was heated at 80° C. for 10 minutes and filtered with Celite, and the filtrate was adjusted to pH 8–8.5 with a saturated aqueous sodium hydrogencarbonate solution and extracted with chloroform. The extract was dried over $Na_2SO_4$, filtered and concentrated in vacuo, and the thus obtained crude product was purified by a silica gel column chromatography (CHCl$_3$:MeOH=40:1) to obtain 161 mg of methyl 8-methyl-3-oxo-8-azabicyclo[3.2.1]-octane-2-carboxylate. The yield was 48.5 mol %. Reaction was carried out in the same manner as above except for using each of lipase A, lipase M, lipase AY, lipase F-AP-15, lipase AK, porcine pancreas lipase (PPL), etc. in place of lipase PS, to give an yield of 30 to 50 mol %. All the reaction products, however, were optically inactive monoester compounds. Colorless needles (a mixture of tautomers and concurrent- ly stereoisomers); Optical purity 0% ee; $^1$H-NMR (CDCl$_3$, 300 MHz): δ 11.8 (s br, 0.2H), 3.89–3.70 (m, 5H), 3.65–3.60 (m, 0.15H), 3.52–3.45 (m, 0.15H), 3.40–3.30 (m, 0.5H), 2.85–2.68 (m, 1H), 2.53 (s, 0.75H), 2.37 (s, 0.3H), 2.35 (s, 2.1H), 2.26–2.05 (m, 3H), 1.92–1.86 (m, 0.5H), 1.82–1.75 (m, 0.5H), 1.64–1.50 (m, 1H); IR (CHCl$_3$): 3689, 1716, 1444, 1303, 1234, 1203 cm$^{-1}$; MS(FAB) m/z 198 (M$^+$+H, 100); HRMS(FAB) $C_{10}H_{16}NO_3$ (M$^+$+H): Calcd. 198.1130, Found 198.1138; Elemental analysis $C_{10}H_{15}NO_3$ Calcd.: C, 60.90; H, 7.67; N, 7.10. Found: C, 60.70; H, 7.73; N, 7.16.

EXAMPLE 6

Synthesis of Methyl (1R,5S)-8-Benzyl-3-oxo-azabicyclo[3.2.1]octane-2-carboxylate ((−)-2b: R'= Bn and R=Me in the Formula (2))

Using each of various enzymes, asymmetric demethoxycarbonylation of dimethyl 8-benzyl-3-oxo-8-azabicyclo [3.2.1]octane-2,4-dicarboxylate was carried out by the following methods (A), (B) and (C).

(A) Synthesis Using Lipase:

According to the method described in Example 5, stirring was conducted for 8 days under the following conditions: PPL 300 mg/100 mg substrate, toluene-0.3 M phosphate buffer (pH=7.2), 35° C. An yield of 28 mol % was attained but the optical purity was 0% ee.

(B) Synthesis Using PLE:

To a solution of dimethyl 8-benzyl-3-oxo-8-azabicyclo [3.2.1]octane-2,4-dicarboxylate (5.00 g, 15.1 mmol) of in 0.1 M phosphate buffer (pH=8.0, 150 ml) was added PLE (794 mg, 1,000 units/mmol), and the resulting mixture was stirred at room temperature for 24 hours. After completion, of the reaction, the reaction mixture was filtered with Celite and the filtrate was extracted with chloroform. The extract was dried over $Na_2SO_4$, filtered and then concentrated in vacuo, and the thus obtained crude product was purified by a silica gel column chromatography (AcOEt:hexane=1:8) to obtain 644 mg of the title compound methyl (1R,5S)-8-benzyl-3-oxo-8-azabicyclo[3.2.1]octane-2-carboxylate. The yield was 20 mol %.

Light-yellow oil (a mixture of tautomers and concurrently stereoisomers); $[α]_D^{26}$ −9.81 (c 1.60, CHCl$_3$); Optical purity 43% ee; $^1$H-NMR (CDCl$_3$, 300 MHz): δ 11.8 (s, 0.4H), 7.42–7.23 (m, 5H), 3.85–3.76 (m, 1H), 3.74 (s, 2H), 3.72 (s, 1H), 3.64 (s, 1.33H), 3.62 (s, 0.67H), 3.61–3.47 (m, 1H), 3.37 (t, J=5.7 Hz, 1H), 3.12 (t, J=2.0 Hz, 0.3H), 2.97–2.90 (m, 0.3H), 2.80–2.69 (m, 1H), 2.32–2.03 (m, 2H), 1.92–1.49 (m, 2H); IR (CHCl$_3$): 3690, 1736, 1713, 1655, 1445, 1350, 1221, 1217 cm$^{-1}$; MS(FAB) m/z 274 (M$^+$+H, 100); HRMS (FAB) $C_{16}H_{21}NO_3$ (M$^+$+H): Calcd. 274.1443, Found 274.1433.

(C) Synthesis Using Baker's Yeast:

To a baker's yeast aqueous solution (50 ml) was added sucrose (4.14 g), and the mixture was stirred at 35° C. for 30 minutes. After the stirring, the thus obtained solution was added to dimethyl 8-benzyl-3-oxo-8-azabicyclo[3.2.1] octane-2,4-dicarboxylate (457 mg, 1.38 mmol) of, and the resulting mixture was stirred at 35° C. for 2 days. After completion of the reaction, the reaction mixture was filtered with Celite and the filtrate was extracted with chloroform. The extract was dried over $Na_2SO_4$, filtered and then concentrated in vacuo, and the thus obtained crude product was purified by a silica gel column chromatography (AcOEt:hexane=1:8) to obtain 61.6 mg of the title compound methyl (1R,5S)-8-benzyl-3-oxo-8-azabicyclo[3.2.1]octane-2-carboxylate. The yield was 16 mol %.

Light-yellow oil; $[\alpha]_D^{19}$+1.94 (c 1.12, $CHCl_3$; Optical purity 6% ee.

In the same manner as above, asymmetric demethoxycarbonylation of each of tropinonedicarboxylic acid methyl esters obtained by converting the amino-protecting group R' of the compounds obtained in Examples 1 to 4 above to a Boc group or a Z group was attempted using each of enzymes such as lipase A, lipase M, lipase AY, lipase F-AP-15, lipase PS, lipase AS, PPL, PLE, B.Y., etc. No optically active tropinonemonocarboxylic acid ester was obtained in any case.

EXAMPLE 7

Synthesis of Diethyl 8-Benzyl-3-oxo-8-azabicyclo [3.2.1]octane-2,4-dicarboxylate (1c: R'=Bn and R= Et in the Formula (1))

To an aqueous solution (30 ml) of 2,5-dimethoxytetrahydrofuran (6.48 ml, 50 mmol) of was added concentrated hydrochloric acid (4 ml), and the resulting mixture was stirred at room temperature for 2.5 hours. After completion of the reaction, the reaction solution was neutralized with potassium carbonate and the excess methanol was evapolated under reduced pressure. The residue was extracted by using an Extrelut column, a column for extraction, with chloroform. The chloroform extract solution was dried over MS4A and magnesium sulfate, filtered and then concentrated in vacuo, whereby a crude product of succindialdehyde was obtained. A methanol (15 ml) solution of benzylamine (9.08 ml, 50 mmol) was added dropwise to a methanol (15 ml) solution of the obtained succindialdehyde in an ice bath, and the reaction mixture was stirred for 2 hours. Then, a methanol (15 ml) solution of diethyl 1,3-acetonedicarboxylate (5.46 ml, 50 mmol) of was added dropwise thereto in an ice bath and the reaction mixture was stirred for additional 16 hours. After completion of the reaction, the solvent was evapolated under reduced pressure and the thus obtained crude product was purified by a silica gel column chromatography (acetone:hexane=1:5) to obtain 14.7 g of the title compound diethyl 8-benzyl-3-oxo-8-azabicyclo[3.2.1]octane-2,4-dicarboxylate. The yield was 82 mol %. Light-yellow oil (a mixture of tautomers and concurrently stereoisomers); $^1$H-NMR ($CDCl_3$, 300 MHz): δ 12.0 (s, 0.25H), 11.9 (s, 0.25H), 7.36–7.24 (m, 5H), 4.32–3.57 (m, 8H), 3.36 (s, 0.33H), 3.31 (s, 0.33H), 3.16 (d, J=2.5 Hz, 0.33H), 2.93 (d, J=1.2 Hz, 0.5H), 2.25–1.77 (m, 4H), 1.34–1.03 (m, 6H); IR ($CHCl_3$): 1732, 1654, 1622, 1321, 1301, 1261, 1230, 1182, 1092 $cm^{-1}$; MS(FAB) m/z 360 ($M^+$+H, 100); HRMS(FAB) $C_{20}H_{26}NO_5$ ($M^+$+H): Calcd. 360.1811, Found 360.1821.

EXAMPLE 8

Synthesis of Diisopropyl 8-Benzyl-3-oxo-8-azabicyclo[3.2.1]octane-2,4-dicarboxylate (1d: R'= Bn and R=i-Pr in the Formula (1))

To an aqueous solution (30 ml) of 2,5-dimethoxytetrahydrofuran (6.48 ml, 50 mmol) was added concentrated hydrochloric acid (4 ml), and the resulting mixture was stirred at room temperature for 2.5 hours. After completion of the reaction, the reaction solution was neutralized with potassium carbonate and the excess methanol was evapolated under reduced pressure. The residue was extracted by using an Extrelut column, a column for extraction, with chloroform. The chloroform extract solution was dried over MS4A and magnesium sulfate, filtered and then concentrated in vacuo, whereby a crude product of succindialdehyde was obtained. Then, dimethyl 1,3-acetonedicarboxylate (7.2 ml, 50 mmol) was added to a sodium isopropoxide solution (38.3 ml) under a nitrogen atmosphere, and the resulting mixture was refluxed for 24 hours. After completion of the reaction, a saturated aqueous ammonium chloride solution was added to the reaction mixture, followed by extraction with AcOEt. The extract was dried over $MgSO_4$, filtered and concentrated in vacuo, whereby a crude product of diisopropyl 1,3-acetonedicarboxylate was obtained.

Under a nitrogen atmosphere, a methanol (15 ml) solution of benzylamine (5.46 ml, 50 mmol) was added dropwise to a methanol (15 ml) solution of the obtained succindialdehyde in an ice bath, and the resulting mixture was stirred for 2 hours. Then, a methanol (15 ml) solution of the obtained diisopropyl 1,3-acetonedicarboxylate was added dropwise thereto in an ice bath and the reaction mixture was stirred for additional 19 hours. After completion of the reaction, the solvent was evapolated under reduced presure and the thus obtained crude product was purified by a silica gel column chromatography (AcOEt:hexane=1:15) to obtain 1.42 g of the title compound diisopropyl 8-benzyl-3-oxo-8-azabicyclo [3.2.1]octane-2,4-dicarboxylate. The yield was 7.3 mol %.

Light-yellow oil (a mixture of tautomers and concurrently stereoisomers); $^1$H-NMR ($CDCl_3$, 300 MHz): δ 12.1 (s, 0.25H), 11.9 (s, 0.25H), 7.41–7.10 (m, 5H), 5.17–4.98 (m, 1.6H), 4.87 (septet, J=6.2 Hz, 0.4H), 4.00–3.55 (m, 4H), 3.37 (s, 0.25H), 3.32 (s, 0.25H), 3.14 (d, J=2.4 Hz, 0.5H), 2.90 (d, J=1.3 Hz, 0.5H), 2.28–1.62 (m, 4H), 1.45–1.17 (m, 10H), 1.14 (d, J=6.3 Hz, 1H), 0.87 (d, J=6.3 Hz, 1H); IR ($CHCl_3$): 3689, 1782, 1652, 1263, 1182, 1103 $cm^{-1}$; MS(FAB) m/z 388 ($M^+$+H, 39); HRMS(FAB) $C_{22}H_{30}NO_5$ ($M^+$+H): Calcd. 388.2124, Found 388.2117.

EXAMPLE 9

Synthesis of Dibutyl 8-Benzyl-3-oxo-8-azabicyclo [3.2.1]octane-2,4-dicarboxylate (1e: R'=Bn and R= n-Bu in the Formula (1))

To an aqueous solution (30 ml) of 2,5-dimethoxytetrahydrofuran (6.48 ml, 50 mmol) was added concentrated hydrochloric acid (4 ml), and the resulting mixture was stirred at room temperature for 2.5 hours. After completion of the reaction, the reaction solution was neutralized with potassium carbonate and the excess methanol was evapolated under reduced pressure. The residue was extracted by using an Extrelut column, a column for extraction, with chloroform. The chloroform extract solution was dried over MS4A and magnesium sulfate, filtered and then concentrated in vacuo, whereby a crude product of succindialdehyde was obtained. Then, dimethyl 1,3-acetonedicarboxylate (7.2 ml, 50 mmol) was added to a sodium butoxide solution (60 ml) under a nitrogen atmosphere, and the resulting mixture was refluxed for 19 hours. After completion of the reaction, a saturated aqueous ammonium chloride solution was added to the reaction mixture, followed by extraction with ethyl acetate. The extract was dried over $MgSO_4$, filtered and concentrated in vacuo, whereby a crude product of dibutyl 1,3-acetonedicarboxylate was obtained.

Under a nitrogen atmosphere, a methanol (15 ml) solution of benzylamine (5.46 ml, 50 mmol) was added dropwise to a methanol (15 ml) solution of the obtained succindialdehyde in an ice bath, and the resulting mixture was stirred for 2 hours. Then, a methanol (15 ml) solution of the obtained dibutyl 1,3-acetonedicarboxylate was added dropwise thereto in an ice bath and the reaction mixture was stirred for additional 13.5 hours. After completion of the reaction, the solvent was evapolated under reduced pressure and the thus obtained crude product was purified by a silica gel column chromatography (AcOEt:hexane=1:15) to obtain 4.77 g of the title compound dibutyl 8-benzyl-3-oxo-8-azabicyclo [3.2.1]octane-2,4-dicarboxylate. The yield was 23 mol %.

Light-yellow oil (a mixture of tautomers and concurrently stereoisomers); $^1$H-NMR (CDCl$_3$, 300 MHz): δ 12.0 (s, 0.2H), 11.8 (s, 0.2H), 7.39–7.24 (m, 5H), 4.22–3.97 (m, 4H), 3.90–3.58 (m, 4H), 3.37 (s, 0.8H), 3.17 (d, J=2.6 Hz, 0.4H), 2.94 (d, J=1.5 Hz, 0.4H), 2.28–1.22 (m, 12H), 0.97–0.84 (m, 6H); IR (CHCl$_3$): 1732, 1654, 1622, 1321, 1301, 1257, 1180 cm$^{-1}$; MS(FAB) m/z 416 (M$^+$+H, 28); HRMS(FAB) C$_{24}$H$_{34}$NO$_5$ (M$^+$+H): Calcd. 416.2451, Found 416.2444.

EXAMPLE 10

Synthesis of Dibenzyl 8-Benzyl-3-oxo-8-azabicyclo [3.2.1]octane-2,4-dicarboxylate (1f: R'=Bn and R= Bn in the Formula (1))

To an aqueous solution (10 ml) of 2,5-dimethoxytetrahydrofuran (1.3 ml, 10 mmol) was added concentrated hydrochloric acid (1 ml), and the resulting mixture was stirred at room temperature for 2.5 hours. After completion of the reaction, the reaction solution was neutralized with potassium carbonate and the excess methanol was evapolated under reduced pressure. The residue was extracted by using an Extrelut column, a column for extraction, with chloroform. The chloroform extract solution was dried over MS4A and magnesium sulfate, filtered and then concentrated in vacuo, whereby a crude product of succindialdehyde was obtained. Then, benzyl alcohol (10.9 ml, 100 mmol) and DMAP (a catalyst) were added to a solution of dimethyl 1,3-acetonedicarboxylate (1.44 ml, 10 mmol) in toluene (30 ml) under a nitrogen atmosphere, and the resulting mixture was refluxed for 5 hours. After completion of the reaction, the excess solvent was evapolated under reduced pressure to obtain a crude product of dibenzyl 1,3-acetonedicarboxylate.

Under a nitrogen atmospere, a solution of benzylamine (1.10 ml, 10 mmol) in benzyl alcohol (5 ml) was added dropwise to a solution of the obtained succindialdehyde in benzyl alcohol (5 ml) in an ice bath, and the reaction mixture was stirred for 2 hours. Then, a solution of the obtained dibenzyl 1,3-acetonedicarboxylate in benzyl alcohol (5 ml) was added dropwise thereto in an ice bath and the resulting mixture was stirred for additional 16 hours. After completion of the reaction, the solvent was evapolated under reduced pressure and the thus obtained crude product was purified by a silica gel column chromatography (AcOEt:hexane=1:15) to obtain 912 mg of the title compound dibenzyl 8-benzyl-3-oxo-8-azabicyclo[3.2.1]octane-2,4-dicarboxylate. The yield was 19 mol %.

Light-yellow oil (a mixture of tautomers and concurrently stereoisomers); $^1$H-NMR (CDCl$_3$, 300 MHz): δ 11.9 (s, 0.25H), 11.8 (s, 0.25H), 7.42–7.12 (m, 15H), 5.27–4.80 (m, 4H), 4.16–3.81 (m, 2H), 3.73–3.50 (m, 2H), 3.39–3.31 (m, 0.5H), 3.24 (d, J=2.5 Hz, 0.5H), 3.00 (d, J=1.4 Hz, 0.5H), 2.28–1.77 (m, 4H); IR (CHCl$_3$): 1733, 1654, 1450, 1259, 1230, 1166 cm$^{-1}$; MS(FAB) m/z 484 (M$^+$+H, 33); HRMS (FAB) C$_{30}$H$_{30}$NO$_5$ (M$^+$+H): Calcd. 484.2124, Found 484.2129.

EXAMPLE 11

Synthesis of Diethyl 8-Benzyloxycarbonyl-3-oxo-8-azabicyclo[3.2.1]octane-2,4-dicarboxylate (1g: R'=Z and R=Et in the Formula (1))

Under a nitrogen atmosphere, benzyloxycarbonyl chloride (0.639 ml, 4.48 mmol) and triethylamine (0.624 ml, 4.48 mmol) were added to a solution in chloroform (20 ml) of the diethyl 8-benzyl-3-oxo-8-azabicyclo[3.2.1]octane-2, 4-dicarboxylate obtained in Example 3, and the resulting mixture was stirred at room temperature for 22 hours. After completion of the reaction, a saturated aqueous sodium chloride solution was added to the reaction mixture, and then extracted with chloroform. The extract was dried over Na$_2$SO$_4$, filtered and then concentrated in vacuo, and the thus obtained crude product was purified by a silica gel column chromatography (AcOEt:hexane=1:10) to obtain 1.32 g of the title compound diethyl 8-benzyloxycarbonyl-3-oxo-8-azabicyclo[3.2.1]octane-2,4-dicarboxylate. The yield was 88 mol %.

Light-yellow oil (a mixture of tautomers and concurrently stereoisomers); $^1$H-NMR (CDCl$_3$, 300 MHz): δ 12.0 (s, 0.1H), 11.8 (s, 0.4H), 7.61–7.28 (m, 5H), 5.23–4.64 (m, 4H), 4.31–4.09 (m, 4H), 4.01–3.84 (m, 0.75H), 3.32 (s br, 0.25H), 3.08 (s br, 0.5H), 2.35–1.82 (m, 3H), 1.72–1.53 (m, 1H), 1.36–1.06 (m, 6H); IR (CHCl$_3$): 3689, 1733, 1701, 1658, 1602, 1472, 1265, 1242, 1180, 1105 cm$^{-1}$; MS(FAB) m/z 404 (M$^+$+H, 65); HRMS(FAB) C$_{21}$H$_{26}$NO$_7$ (M$^+$+H): Calcd. 404.1739, Found 404.1746.

EXAMPLE 12

Synthesis of Ethyl (1R,5S)-8-Benzyl-3-oxo-8-azabicyclo[3.2.1]octane-2-carboxylate ((−)-2c: R'= Bn and R=Et in the Formula (2))

To a solution of diethyl 8-benzyl-3-oxo-8-azabicyclo [3.2.1]octane-2,4-dicarboxylate (993.3 mg, 2.76 mmol) in 0.1 M phosphate buffer (pH=8.0, 27.6 ml) was added PLE (726.3 mg, 5000 units/mmol), and the resulting mixture was stirred at room temperature for 24 hours. After completion of the reaction, the reaction mixture was filtered with Celite and the filtrate was extracted with chloroform. The extract was dried over Na$_2$SO$_4$, filtered and then concentrated in vacuo, and the thus obtained crude product was purified by a silica gel column chromatography (chloroform : methanol=100:1) to obtain 396.4 mg of the title compound ethyl (1R,5S)-8-benzyl-3-oxo-8-azabicyclo[3.2.1]octane-2-carboxylate. The yield was 50 mol %.

Light-yellow oil (a mixture of tautomers and concurrently stereoisomers); $[\alpha]_D^{21}$ −9.09 (c 1.66, CHCl$_3$); Optical purity 93% ee; $^1$H-NMR (CDCl$_3$, 300 MHz): δ 11.9 (s, 0.3H), 7.44–7.22 (m, 5H), 4.29–3.97 (m, 2H), 3.88–3.43 (m, 4H), 3.39–3.36 (m, 0.4H), 3.11 (t, J=2.0 Hz, 0.3H), 2.96–2.89 (m, 0.5H), 2.80–2.60 (m, 1H), 2.31–2.03 (m, 2.5H), 1.92–1.75 (m, 1H), 1.69–1.49 (m, 1H), 1.38–1.04 (m, 3H); IR (CHCl$_3$): 1732, 1714, 1647, 1604, 1301, 1236, 1224 cm$^{-1}$; MS(FAB) m/z 288 (M$^+$+H, 100); HRMS(FAB) C$_{17}$H$_{22}$NO$_3$ (M$^+$+H): Calcd. 288.1599, Found 288.1590.

The same experiment as above was carried out except for changing the stirring time to 3 hours or 48 hours. When the stirring time was 3 hours, the yield was 30 mol % and the optical purity 95% ee. When the stirring time was 48 hours, the yield was 7 mol % and the optical purity 97% ee.

EXAMPLE 13

Synthesis of Isopropyl (1R,5S)-8-Benzyl-3-oxo-8-azabicyclo[3.2.1]octane-2-carboxylate ((−)-2d: R'= Bn and R=i-Pr in the Formula (2))

To a solution in 0.1 M phosphate buffer (pH=8.0, 72 ml) of the diisopropyl 8-benzyl-3-oxo-8-azabicyclo[3.2.1] octane-2,4-dicarboxylate (1d) (1.4 g, 3.61 mmol) obtained in Example 8 was added PLE (950 mg, 5000 units/mmol), and the resulting mixture was stirred at room temperature for 24 hours. After completion of the reaction, the reaction mixture was filtered with Celite and the filtrate was extracted with chloroform. The extract was dried over $Na_2SO_4$, filtered and then concentrated in vacuo, and the thus obtained crude product was purified by a silica gel column chromatography (chloroform:methanol=200:1) to obtain 159 mg of the title compound isopropyl (1R,5S)-8-benzyl-3-oxo-8-azabicyclo[3.2.1]octane-2-carboxylate. The yield was 15 mol % and the optical purity 63% ee.

Light-yellow oil (a mixture of tautomers and concurrently stereoisomers); $[\alpha]_D^{24}$−11.1 (c 1.18, $CHCl_3$); Optical purity 63% ee; $^1$H-NMR ($CDCl_3$, 300 MHz): δ 12.0 (s, 0.3H), 7.43–7.23 (m, 5H), 5.14–4.99 (m, 1H), 3.93–3.49 (m, 4H), 3.45–3.35 (m, 0.9H), 3.11 (t, J=2.1 Hz, 0.3H), 2.89–2.71 (m, 1H), 2.28–2.03 (m, 2.5H), 1.92–1.49 (m, 2H), 1.33–1.14 (m, 6H); IR ($CHCl_3$): 1732, 1716, 1647, 1602, 1284, 1234, 1105 $cm^{-1}$; MS(FAB) m/z 302 ($M^++H$, 34); HRMS(FAB) $C_{18}H_{24}NO_3$ ($M^++H$): Calcd. 302.1757, Found 302.1764.

EXAMPLE 14

Synthesis of Butyl (1R,5S)-8-Benzyl-3-oxo-8-azabicyclo[3.2.1]octane-2-carboxylate ((−)-2e: R'= Bn and R=Bu in the Formula (2))

To a solution in 0.1 M phosphate buffer (pH=8.0, 200 ml) of the dibutyl 8-benzyl-3-oxo-8-azabicyclo[3.2.1]octane-2,4-dicarboxylate (1e) (8.37 g, 20.1 mmol) obtained in Example 9 was added PLE (5.3 g, 5000 units/mmol) of, and the resulting mixture was stirred at room temperature for 24 hours. After completion of the reaction, the reaction mixture was filtered with Celite and the filtrate was extracted with chloroform. The extract was dried over $Na_2SO_4$, filtered and then concentrated in vacuo, and the thus obtained crude product was purified by a silica gel column chromatography (AcOEt:hexane=1:10) to obtain 3.23 g of the title compound butyl (1R,5S)-8-benzyl-3-oxo-8-azabicyclo[3.2.1]octane-2-carboxylate. The yield was 51 mol % and the optical purity 95% ee.

Light-yellow oil (a mixture of tautomers and concurrently stereoisomers); $[\alpha]_D^{25}$−9.38 (c 0.71, $CHCl_3$); Optical purity 95% ee; $^1$H-NMR ($CDCl_3$, 300 MHz): δ 11.9 (s, 0.4H), 7.42–7.21 (m, 5H), 4.23–4.07 (m, 2H), 4.01–3.34 (m, 4.3H), 3.12 (t, J=2.1 Hz, 0.3H), 2.94–2.69 (m, 1H), 2.30–2.04 (m, 2H), 1.92–1.23 (m, 7H), 0.95–0.88 (m, 3H); IR ($CHCl_3$): 1732, 1714, 1647, 1604, 1299, 1234 $cm^{-1}$; MS(FAB) m/z 316 ($M^++H$, 42); HRMS(FAB) $C_{19}H_{26}NO_3$ ($M^++H$): Calcd. 316.1913, Found 316.1905.

EXAMPLE 15

Synthesis of Benzyl (1R,5S)-8-Benzyl-3-oxo-8-azabicyclo[3.2.1]octane-2-carboxylate ((−)-2f: R'= Bn and R=Bn in the Formula (2))

To a solution in 0.1 M phosphate buffer (pH=8.0, 35 ml) of the dibenzyl 8-benzyl-3-oxo-8-azabicyclo[3.2.1]octane-2,4-dicarboxylate (1f) (779 mg, 1.61 mmol) obtained in Example 10 was added PLE (424 mg, 5000 units/mmol), and the resulting mixture was stirred at room temperature for 24 hours. After completion of the reaction, the reaction mixture was filtered with Celite and the filtrate was extracted with chloroform. The extract was dried over $Na_2SO_4$, filtered and then concentrated in vacuo, and the thus obtained crude product was purified by a silica gel column chromatography (chloroform:methanol=100:1) to obtain 287 mg of the title compound benzyl (1R,5S)-8-benzyl-3-oxo-8-azabicyclo[3.2.1]octane-2-carboxylate. The yield was 51 mol % and the optical purity 74% ee.

Light-yellow oil (a mixture of tautomers and concurrently stereoisomers); $[\alpha]_D^{27}$−7.74 (c 1.23, $CHCl_3$); Optical purity 74% ee; $^1$H-NMR ($CDCl_3$, 300 MHz): δ 11.8 (s, 0.1H), 7.47–7.16 (m, 10H), 5.27–4.80 (m, 0.67H), 4.70 (s, 1.33H), 3.92–3.56 (m, 4H), 3.51–3.37 (m, 0.75H), 3.18 (t, J=2.1 Hz, 0.67H), 2.87–2.66 (m, 2H), 2.28–2.02 (m, 2H), 1.93–1.52 (m, 2H); IR ($CHCl_3$): 1735, 1716, 1651, 1612, 1454, 1396, 1298, 1235, 1174, 1166, 1132 $cm^{-1}$; MS(FAB) m/z 350 ($M^++H$, 37); HRMS(FAB) $C_{22}H_{24}NO_3$ ($M^++H$): Calcd. 350.1756, Found 350.1760.

EXAMPLE 16

Synthesis of Ethyl (1R,5S)-8-Benzyloxycarbonyl-3-oxo-8-azabicyclo[3.2.1]octane-2-carboxylate ((−)-2g: R'=Z and R=Et in the Formula (2))

To a solution in 0.1 M phosphate buffer (pH=8.0, 30 ml) of the diethyl 8-benzyloxycarbonyl-3-oxo-8-azabicyclo[3.2.1]octane-2,4-dicarboxylate (1g) (404 mg, 1.00 mmol) obtained in Example 11 was added PLE (263 mg, 5000 units/mmol), and the resulting mixture was stirred at room temperature for 24 hours. After completion of the reaction, the reaction mixture was filtered with Celite and the filtrate was extracted with chloroform. The extract was dried over $Na_2SO_4$, filtered and then concentrated in vacuo, and the thus obtained crude product was purified by a silica gel column chromatography (chloroform:methanol=100:1) to obtain 100 mg of the title compound ethyl (1R,5S)-8-benzyloxycarbonyl-3-oxo-8-azabicyclo[3.2.1]octane-2-carboxylate. The yield was 30 mol %.

Light-yellow oil (a mixture of tautomers and concurrently stereoisomers); $[\alpha]_D^{26}$+0.89 (c 1.08, $CHCl_3$); $^1$H-NMR ($CDCl_3$, 300 MHz): δ 11.9 (s, 0.2H), 7.49–7.27 (m, 5H), 5.22–5.13 (m, 4H), 4.95 (s br, 0.8H), 4.70–4.57 (m br, 0.67H), 4.47 (s br, 0.33H), 4.27–4.20 (m, 2H), 3.27 (s, 1H), 2.43–1.85 (m, 4H), 1.76–1.61 (m, 2H), 1.33–1.06 (m, 3H); IR ($CHCl_3$): 3689, 1697, 1419, 1338, 1321, 1284, 1191, 1099, 1004 $cm^{-1}$; MS(FAB) m/z 332 ($M^++H$, 24); HRMS (FAB) $C_{18}H_{22}NO_5$ ($M^++H$): Calcd. 332.1548, Found 332.1501.

Table 1 summarizes the results of the enzyme-catalyzed asymmetric dealkoxycarbonylations of each tropinonedicarboxylic acid ester which are described in Examples 5 to 16.

Asymmetric dealkoxycarbonylation of tropinonedicarboxylic acid esters

| Example | Substrate | R' | R | Product | Conditions | Enzyme | Time | Yield | Optical purity |
|---|---|---|---|---|---|---|---|---|---|
| 5 | 1a | Me | Me | 2a | A | Lipase[a)] | 3 day | 30–50 mol% | 0% ee |
| 6A | 1b | Bn | Me | 2b | A | PPL[b)] | 8 day | 28 mol% | 0% ee |
| 6B | 1b | Bn | Me | (-)-2b | B | PLE[c)] | 24 hr | 20 mol% | 43% ee |
| 6C | 1b | Bn | Me | (-)-2b | C | B.Y.[d)] | 2 day | 16 mol% | 6% ee |
| 12 | 1c | Bn | Et | — | A | PPL[e)] | 5 day | 0 mol% | — |
| 12 | 1c | Bn | Et | (-)-2c | B | PLE[f)] | 3 hr | 30 mol% | 95% ee |
| 12 | 1c | Bn | Et | (-)-2c | B | PLE[f)] | 24 hr | 50 mol% | 93% ee |
| 12 | 1c | Bn | Et | (-)-2c | B | PLE[f)] | 48 hr | 7 mol% | 97% ee |
| 13 | 1d | Bn | i-Pr | (-)-2d | B | PLE[f)] | 24 hr | 15 mol% | 63% ee |
| 14 | 1e | Bn | n-Bu | (-)-2e | B | PLE[f)] | 24 hr | 34 mol% | 95% ee |
| 15 | 1f | Bn | Bn | (-)-2f | B | PLE[f)] | 24 hr | 51 mol% | 74% ee |
| 16 | 1f | Z | Et | (-)-2g | B | PLE[f)] | 24 hr | 30 mol% | — |

Note)
A: toluene-0.3 M phosphate buffer (pH = 7.2), 35° C.
B: 0.1 M phosphate buffer (pH = 8.0), room temperature
C: baker's yeast (B.Y.): $H_2O$, sucrose, 35° C.
[a)]lipase; lipase A, M, AY, F-AP-15, PS, AK: 2 g/400 mg substrate
[b)]PPL: 300 mg/100 mg substrate
[c)]PLE: 1000 units/mmol substrate
[d)]B.Y.: 3 g/mmol substrate
[e)]PPL: 300 mg/50 mg substrate
[f)]PLE: 5000 units/mmol substrate

EXAMPLE 17

Synthesis of Methyl 8-Benzyl-3-oxo-8-azabicyclo[3.2.1]octane-2-carboxylate (dl-Form)

To a solution dimethyl 8-benzyl-3-oxo-8-azabicyclo[3.2.1]octane-2-carboxylate (23.6 g, 71.2 mmol) in THF (100 ml) was added an aqueous solution (100 ml) of $LiOH.H_2O$ (7.47 g, 178 mmol), and the resulting mixture was stirred at room temperature. After 36 hours, the reaction mixture was adjusted to pH 2 with 2N-HCl and stirred. After 1 day, the stirred reaction mixture was adjusted to pH 8–8.5 with a saturated aqueous sodium hydrogencarbonate solution and extracted with chloroform. The extract was dried over $Na_2SO_4$, filtered and then concentrated in vacuo, and the thus obtained crude product was purified by a silica gel column chromatography (AcOEt:hexane=1:5) to obtain 18.3 g of the title compound methyl 8-benzyl-3-oxo-8-azabicyclo[3.2.1]octane-2-carboxylate. The yield was 94 mol %.

EXAMPLE 18

Synthesis of Methyl 8-Benzyl-8-azabicyclo[3.2.1]octan-2-ene-2-carboxylate (dl-Form)

In an ice bath, $NaBH_4$ (412 mg, 10.6 mmol) was added to a methanol (55 ml) solution of the methyl 8-benzyl-3-oxo-8-azabicyclo[3.2.1]octane-2-carboxylate (1.45 g, 5.32 mmol) obtained in Example 17, and the mixture was stirred for 14.5 hours. After completion of the reaction, a saturated aqueous ammonium chloride solution was added to the reaction mixture and the excess solvent was evapolated under reduced pressure. The residue was adjusted to pH 8.0–8.5 with a saturated aqueous sodium hydrogencarbonate solution and extracted with chloroform. The extract was dried over $Na_2SO_4$, filtered and then concentrated in vacuo, and the resulting residue was dissolved in chloroform (30 ml) under a nitrogen atmosphere. To the resulting solution were added triethylamine (1.48 ml, 10.6 mmol) and DMAP as a catalyst, and trifluoroacetic anhydride (1.13 ml, 7.98 mmol) was added thereto in an ice bath, and then the resulting mixture was stirred at room temperature for 21 hours. After completion of the reaction, the reaction mixture was adjusted to pH 9.0 with a saturated aqueous sodium hydrogencarbonate solution and extracted with chloroform. The extract was dried over $Na_2SO_4$, filtered and then concentrated in vacuo, and the thus obtained crude product was purified by a silica gel column chromatography (AcOEt:hexane=1:8) to obtain 577 mg of the title compound methyl 8-benzyl-8-azabicyclo[3.2.1]octan-2-ene-2-carboxylate. The yield from the above two steps was 42 mol %. The compound obtained in the present example was a dl-form and was used as a reference standard compound for optical purity measurement.

Light-yellow oil; $^1$H-NMR ($CDCl_3$, 300 MHz): δ 7.37–7.21 (m, 5H), 6.90–6.88 (m, 1H), 3.82 (d, J=6.1 Hz, 1H), 3.73 (s, 3H), 3.62 (s, 2H), 3.29–3.26 (m, 1H), 2.66–2.59 (d br, J=20 Hz, 1H), 2.15–2.09 (m, 2H), 1.88–1.78 (m, 2H), 1.54–1.48 (m, 1H); IR ($CHCl_3$): 1705, 1638, 1603, 1437, 1283, 1259, 1086 $cm^{-1}$; MS(FAB) m/z 258 ($M^+$+H, 100); HRMS(FAB) $C_{16}H_{20}NO_2$ ($M^+$+H): Calcd. 258.1509, Found 258.1504.

EXAMPLE 19

Synthesis of Methyl (1R,5S)-8-Benzyl-3-oxo-8-azabicyclo[3.2.1]octane-2-carboxylate ((−)-2b: R'= Bn and R=Me in the Formula (2))

(1) Synthesis from ethyl (1R,5S)-8-benzyl-3-oxo-8-azabicyclo[3.2.1]octane-2-carboxylate ((−)-2c: R'=Bn and R=Et in the formula (2))

Under a nitrogen atmosphere, sodium methoxide (50 ml) was added to ethyl (1R,5S)-8-benzyl-3-oxo-8-azabicyclo[3.2.1]octane-2-carboxylate (113 mg, 0.375 mmol), and the resulting mixture was refluxed for 2 days. After completion of the reaction, a saturated aqueous ammonium chloride solution was added to the reaction mixture and the excess solvent was evapolated under reduced pressure. The residue was adjusted to pH 8.0–8.5 with a saturated aqueous sodium hydrogencarbonate solution and extracted with chloroform.

The extract was dried over Na$_2$SO$_4$, filtered and then concentrated in vacuo, and the thus obtained crude product was purified by a silica gel column chromatography (AcOEt:hexane=1:5) to obtain 1.10 g of the title compound methyl (1R,5S)-8-benzyl-3-oxo-8-azabicyclo[3.2.1]octane-2-carboxylate. The yield was 95 mol %.

(2) In the same manner as above, the title compound methyl (1R,5S)-8-benzyl-3-oxo-8-azabicyclo-[3.2.1]octane-2-carboxylate was obtained also from each of the compounds (−)-2d, (−)-2e and (−)-2f each of which had a substituent different from that of the compound (−)-2b.

EXAMPLE 20

Synthesis of Methyl (1R,5S)-8-Benzyl-8-azabicyclo[3.2.1]octan-2-ene-2-carboxylate (the Compound A in the Reaction Scheme E)

Under a nitrogen atmosphere, NaBH$_4$ (69.6 mg, 1.84 mmol) was added to a methanol (10 ml) solution of the methyl (1R,5S)-8-benzyl-3-oxo-8-azabicyclo[3.2.1]octane-2-carboxylate ((−)-2b) (264 mg, 0.92 mmol) obtained in Example 19, in an ice bath, and the reaction mixture was stirred for 2 hours. After completion of the reaction, a saturated aqueous ammonium chloride solution was added to the reaction mixture and the excess solvent was evapolated under reduced pressure. The residue was adjusted to pH 8.0–8.5 with a saturated aqueous sodium hydrogencarbonate solution and extracted with chloroform. The extract was dried over Na$_2$SO$_4$, filtered and then concentrated in vacuo. Then, the residue was dissolved in chloroform (10 ml) under a nitrogen atmosphere, and triethylamine (267 μl, 1.91 mmol) and DMAP as a catalyst were added thereto. In an ice bath, trifluoroacetic anhydride (203 μl, 1.44 mmol) was added thereto and the resulting mixture was stirred at room temperature for 44 hours. After completion of the reaction, the reaction mixture was adjusted to pH 8.0–8.5 with a saturated aqueous sodium hydrogencarbonate solution and extracted with chloroform. The extract was dried over Na$_2$SO$_4$, filtered and then concentrated in vacuo, and the thus obtained crude product was purified by a silica gel column chromatography (AcOEt:hexane=1:5) to obtain 192.2 mg of the title compound methyl (1R,5S)-8-benzyl-8-azabicyclo[3.2.1]octan-2-ene-2-carboxylate. The yield from the above two steps was 81 mol %.

Light-yellow oil; $[\alpha]_D^{23}$−17.8 (c 0.71, CHCl$_3$); Optical purity 95% ee; Chiral HPLC analysis [DAICEL CHIRALCEL OD(25×0.46); eluent: n-hexane/2-propanol=100/1; flow rate: 0.3 ml/min; temperature: 25° C.; detector: 254 nm; (−)-A; 34.3 min, (+)-A; 38.0 min]

$^1$H-NMR (CDCl$_3$, 300 MHz): δ 7.37–7.21 (m, 5H), 6.90–6.88 (m, 1H), 3.82 (d, J=6.1 Hz, 1H), 3.73 (s, 3H), 3.62 (s, 2H), 3.29–3.26 (m, 1H), 2.66–2.59 (d br, J=20 Hz, 1H), 2.15–2.09 (m, 2H), 1.88–1.78 (m, 2H), 1.54–1.48 (m, 1H); IR (CHCl$_3$): 1705, 1638, 1603, 1437, 1283, 1259, 1086 cm$^{-1}$; MS(FAB) m/z 258 (M$^+$+H, 100); HRMS(FAB) C$_{16}$H$_{20}$NO$_2$ (M$^+$+H): Calcd. 258.1509, Found 258.1504.

EXAMPLE 21

Synthesis of Methyl (1R,5S)-8-Methyl-3-oxo-8-azabicyclo[3.2.1]octane-2-carboxylate (the Compound (+)-B in the Reaction Scheme F)

To a solution of methyl (1R,5S)-8-benzyl-3-oxo-8-azabicyclo[3.2.1]octane-2-carboxylate ((−)-2b) (818 mg, 2.99 mmol) in acetic acid (10 ml) was added 10% Pd-C (a catalyst), and the resulting mixture was stirred under a hydrogen atmosphere for 10 hours. After completion of the reaction, the mixture was filtered with Celite and the filtrate was concentrated in vacuo. The residue was adjusted to pH 8.0–8.5 with a saturated aqueous sodium hydrogencarbonate solution and extracted with chloroform. The extract was dried over Na$_2$SO$_4$, filtered and then concentrated in vacuo, and the thus obtained crude product was purified by a silica gel column chromatography (CHCl$_3$:MeOH=30:1) to obtain 536.5 mg of methyl (1R,5S)-3-oxo-8-azabicyclo[3.2.1]octane-2-carboxylate. In this case, the yield was 98 mol %. Then, to a methanol (20 ml) solution of this compound (281 mg, 1.54 mmol) were added a 37% formaldehyde solution (213 μl, 7.67 mmol), formic acid (579 μl, 15.4 mmol) and paraformaldehyde (200 mg), and the resulting mixture was refluxed for 17 hours. After completion of the reaction, the reaction mixture was adjusted to pH 8.0–8.5 with a saturated aqueous sodium hydrogencarbonate solution and extracted with chloroform. The extract was dried over Na$_2$SO$_4$, filtered and then concentrated in vacuo, and the thus obtained crude product was purified by a silica gel column chromatography (CHCl$_3$:MeOH=50:1) to obtain 274 mg of methyl (1R,5S)-8-methyl-3-oxo-8-azabicyclo[3.2.1]octane-2-carboxylate. The yield from the above two steps was 88 mol %.

Light-yellow oil; $[\alpha]_D^{22}$+19.4 (c 0.47, MeOH).

EXAMPLE 22

Synthesis of Methyl (1R,5S)-8-t-Butoxycarbonyl-3-oxo-8-azabicyclo[3.2.1]octane-2-carboxylate ((−)-2h: R'=Boc and R=Me in the Formula (2))

To a solution in acetic acid (5 ml) of the methyl (1R,5S)-8-benzyl-3-oxo-8-azabicyclo[3.2.1]octane-2-carboxylate ((−)-2b) (188 mg, 0.69 mmol) obtained in Example 19 was added 10% Pd-C (a catalyst), and the resulting mixture was stirred under a hydrogen atmosphere for 7 hours. After completion of the reaction, the mixture was filtered with Celite and the solvent was evapolated under reduced pressure. The residue was adjusted to pH 8.0–8.5 with a saturated aqueous sodium hydrogencarbonate solution and extracted with chloroform. The extract was dried over Na$_2$SO$_4$, filtered and then concentrated in vacuo, and the resulting residue was dissolved in chloroform. Di-t-butyl dicarbonate (156 μl, 0.677 mmol) and triethylamine (94.4 μl, 0.677 mmol) were added thereto, and the resulting mixture was stirred at room temperature for 4 hours. After completion of the reaction, a saturated aqueous sodium chloride solution was added to the reaction mixture, and then extracted with chloroform. The extract was dried over Na$_2$SO$_4$, filtered and then concentrated in vacuo, and the thus obtained crude product was purified by a silica gel column chromatography (AcOEt:hexane=1:8) to obtain 127 mg of the title compound methyl (1R,5S)-8-t-butoxycarbonyl-3-oxo-8-azabicyclo[3.2.1]octane-2-carboxylate. The yield from the above two steps was 73 mol %.

Light-yellow oil; $[\alpha]_D^{27}$−30.9 (c 0.78, CHCl$_3$); $^1$H-NMR (CDCl$_3$, 300 MHz): δ 11.8 (s, 0.33H), 4.85 (s br, 1H), 4.36 (m br, 1H), 3.78 (s, 1H), 3.77 (s, 1H), 3.71 (s, 1H), 3.26 (s, 0.33H), 3.09–3.01 (m, 0.67H), 2.42–1.81 (m, 3.67H), 1.70–1.56 (m, 2H), 1.51 (s, 2H), 1.47 (s, 3.5H), 1.45 (s, 3.5H); MS(FAB) m/z 283 (M$^+$+H, 18); IR (CH$_3$Cl): 1811, 1755, 1691, 1396, 1373, 1340, 1315, 1286, 1261, 1226, 1203, 1164, 1120, 1074 cm$^{-1}$; HRMS(FAB) C$_{14}$H$_{22}$NO$_5$ (M$^+$+H): Calcd. 284.1498, Found 284.1493.

EXAMPLE 23

Synthesis of Methyl (1R,5S)-8-t-Butoxycarbonyl-8-azabicyclo[3.2.1]octan-2-ene-2-carboxylate ((−)-6a: R'=Boc and R=Me in the Formula (6))

Under a nitrogen atmosphere, NaBH$_4$ (6.84 mg, 0.18 mmol) was added to a methanol (3 ml) solution of the methyl (1R,5S)-8-t-butoxycarbonyl-3-oxo-8-azabicyclo[3.2.1]octane-2-carboxylate ((−)-2h) (25.6 mg, 0.09 mmol) obtained in Example 22, in an ice bath, and the reaction mixture was stirred for 3 hours. After completion of the reaction, a saturated aqueous ammonium chloride solution was added to the reaction mixture and the excess solvent was evapolated under reduced pressure. The residue was adjusted to pH 8.0–8.5 with a saturated aqueous sodium hydrogencarbonate solution and extracted with chloroform. The extract was dried over $Na_2SO_4$, filtered and then concentrated in vacuo. Then, the residue was dissolved in chloroform (10 ml) under a nitrogen atmosphere, and triethylamine (50.4 μl, 0.361 mmol) and DMAP (a catalyst) were added thereto. In an ice bath, trifluoroacetic anhydride (25.5 μl, 0.181 mmol) was added thereto and the resulting mixture was stirred at room temperature for 36 hours. After completion of the reaction, the reaction mixture was adjusted to pH 8.0–8.5 with a saturated aqueous sodium hydrogencarbonate solution and extracted with chloroform. The extract was dried over $Na_2SO_4$, filtered and then concentrated in vacuo, and the thus obtained crude product was purified by preparative-TLC (AcOEt:hexane=1:2) to obtain 6.8 mg of the title compound methyl (1R,5S)-8-t-butoxycarbonyl-8-azabicyclo[3.2.1]octan-2-ene-2-carboxylate. The yield from the above two steps was 28 mol %. The optical rotatory power of the methyl (1R,5S)-8-t-butoxycarbonyl-8-azabicyclo[3.2.1]octan-2-ene-2-carboxylate obtained here is in good agreement with the value described in literature, $[\alpha]_D^{21}$ −52.4 (c 1.00, $CHCl_3$). By the purification by preparative-TLC for separation, an optical purity of 95% ee was attained, and the compound was colorless needles (mp 79–80° C.) and could easily be further increased in optical purity by purification by recrystallization. Colorless needles; mp 79–80° C. (AcEt/hexane=1/4); $[\alpha]_D^{26}$ −60.2 (c 1.63, $CHCl_3$); Optical purity 95% ee; Chiral HPLC analysis [DAICEL CHIRALCEL OD(25× 0.46); eluent: n-hexane/2-propanol=100/1; flow rate: 0.5 ml/min; temperature: 25° C.; detector: 254 nm; (−)-6a; 20.5 min, (+)-6a; 24.9 min]; $^1$H-NMR ($CDCl_3$, 300 MHz): δ 6.78–6.75 (m, 1H), 4.83–4.78 (m, 1H), 4.37–4.28 (m, 1H), 3.78 (s, 3H), 2.89–2.81 (m, 1H), 2.20–1.87 (m, 4H), 1.65–1.53 (m, 1H), 1.44 (s, 9H); IR (KBr): 1716, 1701, 1641, 1442, 1419, 1380, 1369, 1340, 1323, 1259, 1224, 1164, 1105, 1089 cm$^{-1}$; MS(FAB) m/z 268 (M$^+$+H, 19); HRMS(FAB) $C_{14}H_{22}NO_4$ (M$^+$+H): Calcd. 268.1548, Found 268.1552; Elemental analysis $C_{14}H_{21}NO_4$ Calcd.: C, 62.90; H, 7.92; N, 5.24. Found: C, 62.69; H, 7.90; N, 5.53.

EXAMPLE 24

Synthesis of Methyl (1R,5S)-8-Methyl-8-azabicyclo[3.2.1]octan-2-ene-2-carboxylate ((−)-6b: R'=Me and R=Me in the Formula (6))

Under a nitrogen atmosphere, trifluoroacetic acid (TFA) (15 μl, 0.196 mmol) was added to a solution in $CH_2Cl_2$ (2 ml) of the methyl (1R,5S)-8-t-butoxycarbonyl-8-azabicyclo[3.2.1]octan-2-ene-2-carboxylate ((−)-6a) (26.2 mg, 0.098 mmol) obtained in Example 23, in an ice bath, and the resalting mixture was stirred for 3 hours in an ice bath. After completion of the reaction, the excess solvent was evapolated under reduced pressure and the residue was dissolved in methanol (3 ml). Then, formaldehyde (a 37% aqueous solution, 22 μl, 0.294 mmol), formic acid (18 μl, 0.490 mmol) and paraformaldehyde (20 mg) as catalyst were added thereto, and the resulting mixture was refluxed for 4 hours. After the excess solvent was evapolated under reduced pressure, the residue was adjusted to pH 8.0 with a saturated aqueous sodium hydrogencarbonate solution and extracted with chloroform. The extract was dried over $Na_2SO_4$, filtered and then concentrated in vacuo, and the thus obtained crude product was purified by prepartive-TLC for separation ($CHCl_3$:MeOH=10:1) to obtain 6.9 mg of the title compound methyl (1R,5S)-8-methyl-8-azabicyclo[3.2.1]octan-2-ene-2-carboxylate. The yield was 38.8 mol %.

Light-yellow oil; $[\alpha]_D^{21}$ −41.0 (c 0.85, MeOH); $^1$H-NMR ($CDCl_3$, 300 MHz): δ 6.83–6.81 (m, 1H), 3.79 (d, J=5.4 Hz, 1H), 3.74 (s, 3H), 3.25 (dd, J=3.0 and 2.5 Hz, 1H), 2.66–2.59 (m, 1H), 2.35 (s, 3H), 2.27–2.11 (m, 2H), 1.90–1.80 (m, 2H), 1.55–1.48 (m, 1H); IR ($CHCl_3$): 1708, 1641, 1439, 1363, 1284, 1263 cm$^{-1}$; MS(FAB) m/z 290 (M$^+$+H, 39); HRMS (FAB) $C_{10}H_{16}NO_2$ (M$^+$+H): Calcd. 182.1181, Found 182.1176.

INDUSTRIAL APPLICABILITY

According to the present invention, an optically active tropinonemonocarboxylic acid ester derivative useful as an intermediate for synthesis of optically active tropane derivatives was obtained by reacting succindialdehyde with an organic amine and acetonedicarboxylic acid to obtain a tropinonedicarboxylic acid ester derivative, and then subjecting this derivative to enzyme-catalyzed asymmetric dealkoxycarbonylation. Since anhydroecgonine methyl ester derived from the optically active tropinonemonocarboxylic acid ester derivative by reduction and dehydration had the same direction of optical rotation as in the case of anhydroecgonine methyl ester obtained from natural cocaine, it was proved that the optically active tropinonemonocarboxylic acid ester derivative obtained had the same absolute configuration as that of natural cocaine. The yield of the optically active tropinonemonocarboxylic acid ester derivative from the asymmetric dealkoxycarbonylation was 30 to 50 mol %, and its optical purity was 70 to 97% ee. In addition, it was found that a crystalline optically active anhydroecgonine carboxylic acid ester derivative can be obtained by reducing and then dehydrating the optically active tropinonemono-carboxylic acid ester derivative and that its optical purity can easily be increased by recrystallization. It was revealed that such an optically active tropinonemono-carboxylic acid ester derivative obtained according to the present invention is useful as an intermediate for synthesis of 2-β-carbomethoxy-3-β-phenyltropane, 2-β-carbomethoxy-3-β-(4-iodophenyl)-tropane, 2-β-carbomethoxy-3-β-(4-iodophenyl)-8-(3-fluoropropyl) nortropane and tropane alkaloids such as (−)-ferruginine, (+)-knightinol, etc.

What is claimed is:

1. A process for producing an optically active tropinonemonocarboxylic acid ester compound which comprises subjecting a tropinonedicarboxylic acid ester compound represented by the following formula (1):

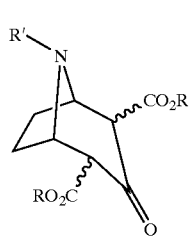

(1)

wherein R' is an alkyl group, an aralkyl group or an amino-protecting group selected from lower aliphatic acyl groups, aromatic acyl groups, lower alkoxycarbonyl groups, aralkyloxycarbonyl groups, aryloxycarbonyl groups and tri-lower-alkylsilyl groups, and R is an alkyl group or an aralkyl group, to asymmetric dealkoxycarbonylation in the presence of an enzyme to obtain an optically active tropinonemonocarboxylic acid ester compound represented by the following formula (2):

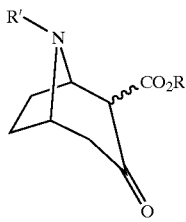

(2)

wherein R and R' are as defined above.

2. A process for producing an optically active tropinonemonocarboxylic acid ester compound according to claim 1, wherein the enzyme is liver esterase or baker's yeast.

3. A process for producing an optically active tropinonemonocarboxylic acid ester compound according to claim 1 or 2, wherein R is an alkyl group of 1 to 6 carbon atoms and R' is an aralkyl group, a lower aliphatic acyl group, an aromatic acyl group, an aryloxycarbonyl group or a tri-lower-alkylsilyl group; or R is an alkyl group of 2 to 6 carbon atoms and R' is an aralkyloxycarbonyl group; or each of R and R' is an aralkyl group.

4. A process for producing an optically active tropinonemonocarboxylic acid ester compound according to any one of claims 1 or 2, wherein R is an alkyl group of 1 to 6 carbon atoms selected from methyl group, ethyl group, propyl group, isopropyl group, butyl group, isobutyl group, s-butyl group, t-butyl group, pentyl group, isopentyl group, neopentyl group, t-pentyl group and hexyl group, and R' is an aralkyl group of 7 to 10 carbon atoms selected from benzyl group, phenethyl group, phenylpropyl group and phenylbutyl group; or R is an alkyl group of 2 to 6 carbon atoms selected from ethyl group, propyl group, isopropyl group, butyl group, isobutyl group, s-butyl group, t-butyl group, pentyl group, isopentyl group, neopentyl group, t-pentyl group and hexyl group, and R' is an aralkyloxycarbonyl group of 8 or 9 carbon atoms selected from benzyloxycarbonyl group and methoxybenzyloxycarbonyl group; or each of R and R' is an aralkyl group of 7 to 10 carbon atoms selected from benzyl group, phenethyl group, phenylpropyl group and phenylbutyl group.

5. A process for producing an optically active tropinonemonocarboxylic acid ester compound which comprises reacting succindialdehyde represented by the following formula (3):

(3)

with an organic amine represented by the following formula (4):

(4)

wherein R" is an alkyl group or an aralkyl group, and an acetonedicarboxylic acid ester represented by the following formula (5):

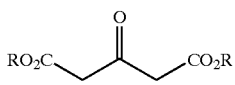

(5)

wherein R is an alkyl group or an aralkyl group; if necessary, converting the substituent derived from the substituent R" of the organic amine of the formula (4) to an amino-protecting group; thereby obtaining a tropinonedicarboxylic acid ester compound represented by the following formula (1):

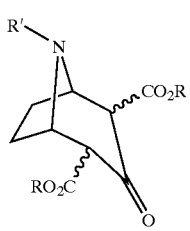

(1)

wherein R' is an alkyl group, an aralkyl group or an amino-protecting group selected from lower aliphatic acyl groups, aromatic acyl groups, lower alkoxycarbonyl groups, aralkyloxycarbonyl groups, aryloxycarbonyl groups and tri-lower-alkylsilyl groups, and R is an alkyl group or an aralkyl group; and then subjecting the tropinonedicarboxylic acid ester compound of formula (1) to asymmetric dealkoxycarbonylation in the presence of an enzyme to obtain an optically active tropinonemonocarboxylic acid ester compound represented by the following formula (2):

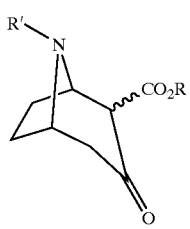

(2)

wherein R and R' are as defined above.

6. A process for producing an optically active tropinonemonocarboxylic acid ester compound according to claim 5, wherein the enzyme is liver esterase or baker's yeast.

7. A process for producing an optically active tropinonemonocarboxylic acid ester derivative according to claim 5 or 6, wherein in the above formula (1), R is an alkyl group of 1 to 6 carbon atoms and R' is an aralkyl group, a lower aliphatic acyl group, an aromatic acyl group, an aryloxycarbonyl group or a tri-lower-alkylsilyl group; or R is an alkyl group of 2 to 6 carbon atoms and R' is an aralkyloxycarbonyl group; or each of R and R' is an aralkyl group.

8. A process for producing an optically active tropinonemonocarboxylic acid ester compound according to any one of claims 5 or 6, wherein R is an alkyl group of 1 to 6 carbon atoms selected from methyl group, ethyl group, propyl group, isopropyl group, butyl group, isobutyl group, s-butyl group, t-butyl group, pentyl group, isopentyl group, neopentyl group, t-pentyl group and hexyl group, and R' is an aralkyl group of 7 to 10 carbon atoms selected from benzyl group, phenethyl group, phenylpropyl group and phenylbutyl group; or R is an alkyl group of 2 to 6 carbon atoms selected from ethyl group, propyl group, isopropyl group, butyl group, isobutyl group, s-butyl group, t-butyl group, pentyl group, isopentyl group, neopentyl group, t-pentyl group and hexyl group, and R' is an aralkyloxycarbonyl group of 8 or 9 carbon atoms selected from benzyloxycarbonyl group and methoxybenzyloxycarbonyl group; or each of R and R' is an aralkyl group of 7 to 10 carbon atoms selected from benzyl group, phenethyl group, phenypropyl group and phenylbutyl group.

9. A process for producing an optically active tropinonemonocarboxylic acid ester compound according to claim 3, wherein R is an alkyl group of 1 to 6 carbon atoms selected from methyl group, ethyl group, propyl group, isopropyl group, butyl group, isobutyl group, s-butyl group, t-butyl group, pentyl group, isopentyl group, neopentyl group, t-pentyl group and hexyl group, and R' is an aralkyl group of 7 to 10 carbon atoms selected from benzyl group, phenethyl group, phenylpropyl group and phenylbutyl group; or R is an alkyl group of 2 to 6 carbon atoms selected from ethyl group, propyl group, isopropyl group, butyl group, isobutyl group, s-butyl group, t-butyl group, pentyl group, isopentyl group, neopentyl group, t-pentyl group and hexyl group, and RW is an aralkyloxycarbonyl group of 8 or 9 carbon atoms selected from benzyloxycarbonyl group and methoxybenzyloxycarbonyl group; or each of R and R' is an aralkyl group of 7 to 10 carbon atoms selected from benzyl group, phenethyl group, phenylpropyl group and phenylbutyl group.

10. A process for producing an optically active tropinonemonocarboxylic acid ester compound according to claim 7, wherein R is an alkyl group of 1 to 6 carbon atoms selected from methyl group, ethyl group, propyl group, isopropyl group, butyl group, isobutyl group, s-butyl group, t-butyl group, pentyl group, isopentyl group, neopentyl group, t-pentyl group and hexyl group, and R' is an aralkyl group of 7 to 10 carbon atoms selected from benzyl group, phenethyl group, phenylpropyl group and phenylbutyl group; or R is an alkyl group of 2 to 6 carbon atoms selected from ethyl group, propyl group, isopropyl group, butyl group, isobutyl group, s-butyl group, t-butyl group, pentyl group, isopentyl group, neopentyl group, t-pentyl group and hexyl group, and R' is an aralkyloxycarbonyl group of 8 or 9 carbon atoms selected from benzyloxycarbonyl group and methoxybenzyloxycarbonyl group; or each of R and R' is an aralkyl group of 7 to 10 carbon atoms selected from benzyl group, phenethyl group, phenylpropyl group and phenylbutyl group.

* * * * *